US008586300B2

(12) United States Patent
Zeisel et al.

(10) Patent No.: US 8,586,300 B2
(45) Date of Patent: Nov. 19, 2013

(54) GENETIC POLYMORPHISMS AND INFERTILITY

(75) Inventors: Steven H. Zeisel, Chapel Hill, NC (US); Amy Johnson, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 291 days.

(21) Appl. No.: 12/934,236

(22) PCT Filed: Mar. 25, 2009

(86) PCT No.: PCT/US2009/038221
§ 371 (c)(1),
(2), (4) Date: Oct. 26, 2010

(87) PCT Pub. No.: WO2009/120763
PCT Pub. Date: Oct. 1, 2009

(65) Prior Publication Data
US 2011/0034476 A1 Feb. 10, 2011

Related U.S. Application Data

(60) Provisional application No. 61/039,217, filed on Mar. 25, 2008.

(51) Int. Cl.
C12Q 1/68 (2006.01)
C12P 19/34 (2006.01)
C07H 21/02 (2006.01)

(52) U.S. Cl.
USPC .......................................... 435/6.1; 435/91.2

(58) Field of Classification Search
None
See application file for complete search history.

(56) References Cited

PUBLICATIONS da Costa K. et al. Jul. 2006, The FASEB Journal, vol. 20, No. 9, pp. 1336-1344.*
Pennisi E. Science; Sep. 18, 1998; 281, 5384, p. 1787-1789.*
Hegele R.A. Arterioscler Thromb Vasc Biol. 2002;22:1058-1061.*
Lucentini J. The Scientist, Dec. 20, 2004, p. 20.*
Wall J.D. et al. Nature Reviews (Aug. 2004), vol. 4, p. 587-597.*
Zill P. et al. Molecular Psychiatry (2004) 9, 1030-1036.*
GeneCards output for CHDH gene, from www.genecards.org, printed on Jan. 14, 2013, pp. 1-17.*
da Costa K.-A. The FASEB Journal, vol. 20, Jul. 2006, pp. 1336-1344.*
Juppner H. Bone vol. 17, No. 2, Supplement, Aug. 1995:39S-42S.*
Zeisel S.H. IUBMB Life, 59(6): 380-387, Jun. 2007.*
Johnson A.R. et al. 2012 PLoS ONE 7(4):e36047, pp. 1-12.*
Wang et al., "Gut flora metabolism of phosphatidylcholine promotes cardiovascular disease," Nature, vol. 472, pp. 57-65 (Apr. 7, 2011).
Schwahn et al., "Homocysteine-betaine interactions in a murine model of 5,10-methylenetetrahydrofolate reductase deficiency," The FASEB Journal express article 10.1096/fj.02-0456fje. Published online Jan. 22, 2003.
Patterson et al., "USDA Database for the Choline Content of Common Foods—Release Two," U.S. Department of Agriculture Research Service, Beltsville Human Nutrition Research Center, Nutrient Data Laboratory (Jan. 2008).
Flower et al., "Metabolism and Transfer of Choline in Hamster Small Intestine,"J. Physiol., vol. 226, pp. 473-489 (1972).
Detopoulou et al., "Dietary choline and betaine intakes in relation to concentrations of inflammatory markers in healthy adults: the ATTICA study,"Am. J. Clin. Nutr., vol. 87, pp. 424-430 (2008).
Craig, Stuart, "Betaine in human nutrition1,2," Am. J. Clin. Nutr., vol. 80, pp. 539-549 (2004).
"Choline and Betaine for Animal Nutrition," 09BLCM-CHOLINEBETAINESHEET—Sep. 2009, Balchem Corp. (2009).
Dhillon et al., "Associations of MTHFR DNMT3b4977bp deletion in mtDNA and GSTM1 deletion, and aberrant CpG island hypermethylation of GSTM1 in non-obstructive infertility in Indian men," Molecular Human Reproduction, vol. 13, pp. 213-222 (Feb. 2, 2007).
GenBank Accession No. NC_000001, Jun. 10, 2009.
GenBank Accession No. NC_000003, Jun. 10, 2009.
GenBank Accession No. NC_000004, Jun. 10, 2009.
GenBank Accession No. NC_000005, Jun. 10, 2009.
GenBank Accession No. NC_000007, Jun. 10, 2009.
GenBank Accession No. NC_000009, Jun. 10, 2009.
GenBank Accession No. NC_000011, Jun. 10, 2009.
GenBank Accession No. NC_000014, Jun. 10, 2009.
GenBank Accession No. NC_000017, Jun. 10, 2009.
GenBank Accession No. NC_000022, Jun. 10, 2009.
International Search Report corresponding to International Application No. PCT/US2009/038221 dated Dec. 17, 2009.
Ivanov et al., "Genetic Variants in Phosphatidyletanolamine N-methyltranferase and Methylenetetrahydrofolate Dehydrogenase Influence Biomarkers of Choline Metabolism when Folate Intake is Restricted," Journal of the American Dietetic Association, vol. 109, Feb. 2009.
Kelly, T. L., O. R. Neaga, et al. (2005). "Infertility in 5,10-methylenetetrahydrofolate reductase (MTHFR)-deficient male mice is partially alleviated by lifetime dietary betaine supplementation." Biol Reprod 72(3): 66-77.
Niculescu et al., "Lymphocyte gene expression in subjects fed a low-choline diet differs between those who develop organ dysfunction and those who do not," Am. J. Clin. Nutr., vol. 86, pp. 230-239 (2007).

(Continued)

Primary Examiner — Stephen Kapushoc
(74) Attorney, Agent, or Firm — Jenkins, Wilson, Taylor & Hunt, P.A.

(57) ABSTRACT

Methods of screening for a cause of low sperm motility and/or for mitochondrial impairment in subjects are provided, comprising determining a genotype of the subject with respect to at least one choline metabolism gene and comparing the genotype of the subject with at least one reference choline metabolism genotype associated with low sperm motility and/or impaired mitochondrial function, wherein a similarity between the subject and reference genotypes indicates a cause of low sperm motility and/or impaired mitochondrial function in the subject. In another aspect, methods for treating subjects having low sperm motility and/or impaired mitochondrial function are provided, comprising administering to the subject an effective amount of a choline metabolism supplement composition to at least partially ameliorate the low sperm motility and/or impaired mitochondrial function.

1 Claim, 17 Drawing Sheets

(56) References Cited

PUBLICATIONS

Adham et al., "Teratozoospermia in mice lacking the transition protein 2 (Tnp2)." Mol Hum Reprod 7, 513-520 (2001).

Boehm et al. "Clinical chemistry reference database for Wistar rats and C57/BL6 mice." Biol Chem 388, 547-554 (2007).

Buchman et al. "Choline deficiency: a cause hepatic steatosis during parenteral nutrition that can be reversed with intravenous supplementation." Hepatology 22, 1399-1403 (1995).

Chern et al. "Betaine aldehyde, betaine, and choline levels in rat livers during ethanol metabolism." Biochem Pharmacol 60(11), 1629-37 (2000).

Ford, W. C. "Glycolysis and sperm motility: does a spoonful of sugar help the flagellum go round?" Hum Reprod Update 12(3), 269-74 (2006).

Fox et al. "*Helicobacter hepaticus* sp. nov., a microerophilic isolated from livers and intestinal mucosal scrapings from mice." J Clin Microbiol 32, 1238-1245 (1994).

Frezza et al. "Organelle isolation: functional mitochondria from mouse liver, muscle and cultured fibroblasts." Nat Protoc 2(2), 287-95 (2007).

Ikuta et al. "Oxidative pathway of choline to betaine in the soluble fraction prepared from *Arthrobacter globiformis*." J Biochem 82(1), 157-63 (1977).

Jacobsen, D. "Determinants of hyperhomocysteinemia: a matter of nature and nurture." Am J Clin Nutr 64(4), 641-642 (1996).

Kagawa et al. "Control of choline oxidation in liver mitochondria by adenine nucleotides." J. Biol. Chem. 240, 1836-1842 (1965).

Koc et al. "Quantitation of choline and its metabolites in tissues and foods by liquid chromatography/electrospray ionization-isotope dilution mass spectrometry." Anal Chem 74, 4734-4770 (2002).

Lawson-Yuen et al. "The use of betaine in the treatment of elevated homocysteine." Mol Genet Metab 88, 201-207 (2006).

Maconochie et al. "Infertility among male UK veterans of the 1990-1 Gulf war: reproductive cohort study." BMJ 329, 196-201 (2004).

Narvaiza et al. "Effect of adenovirus-mediated RNA interference on endogenous microRNAs in a mouse model of multidrug resistance protein 2 gene silencing." J Virol 80, 12236-12247 (2006).

Nasr-Esfahani et al. "Sperm MTT viability assay: a new method for evaluation of human sperm-viability." J Assist Reprod Genet 19, 477-482 (2002).

Ohta-Fukuyama et al. "Identification and properties of the prosthetic group of choline oxidase from *Alcaligenes* sp."J Biochem 88(1), 197-203 (1980).

Pomfret et al. "Measurement of choline and choline metabolite concentrations using high-pressure liquid chromatography and gas chromatography-mass spectrometry." Anal. Biochem. 180, 85-90 (1989).

Rajapakse et al. "Isolation and characterization of intact mitochondria from neonatal rat brain." Brain Res Brain Res Protoc 8(3), 176-83 (2001).

Resseguie et al. "Phosphatidylethanolamine n-methyltransferase (PEMT) gene expression is induced by estrogen in human and mouse primary hepatocyte." FASEB J 21, 2622-2632 (2007).

Rozwadowski et al. "Choline oxidase, a catabolic enzyme in *Arthrobacter pascens*, facilitates adaptation to osmotic stress in *Escherichia coli*." J Bacteriol 173(2), 472-8 (1991).

Schwahn et al. "Betaine rescue of an animal with methylenetetrahydrofolate reductase deficiency." Biochem J 382(Pt 3), 831-40 (2004).

Schwahn et al. "Homocysteine-betaine interactions in a murine model of 5,10-methylenetetrahydrofolate reductase deficiency." Faseb J 17(3), 512-4 (2003).

Shames et al. "Identification of widespread *Helicobacter hepaticus* infection in feces in commercial mouse colonies by culture and PCR assay." J Clin Microbiol 33, 2968-2972 (1995).

Steenge et al. "Betaine supplementation lowers plasma homocysteine in healthy men and women." J Nutr 133, 1291-1295 (2003).

Thonneau et al. "Incidence and main causes of infertility in a resident population (1,850,000) of three French regions (1988-1989)." Human reproduction 6, 811-816 (1991).

Tsuge et al. "A novel purification and some properties of rat liver mitochondrial choline dehydrogenase." Biochim Biophys Acta 614(2): 274-84 (1980).

Turner, R. M. "Tales from the tail: what do we really know about sperm motility?" J Androl 24(6), 790-803 (2003).

Ventela et al. "Intercellular organelle traffic through cytoplasmic bridges in early spermatids of the rat: mechanisms of haploid gene product sharing."Mol Biol Cell 14(7), 2768-80 (2003).

Wang et al. "Knockout of Mkp-1 enhances the host inflammatory responses to gram-positive bacteria." J Immunol 178, 5312-5320 (2007).

Wendel et al. "Betaine in the treatment of homocystinuria due to 5,10-methylenetetrahydro-folate reductase deficiency." Eur. J. Pediatr. 142, 147-150 (1984).

Yao et al. "The active synthesis of phosphatidylcholine is required for very low density lipoprotein secretion from rat hepatocytes." J. Biol. Chem. 263, 2998-3004 (1988).

Zeisel, S.H. "Choline: Critical Role During Fetal Development and Dietary Requirements in Adults." Annu Rev Nutr. 26, 229-250 (2006).

Zeisel et al. "Choline, an essential nutrient for humans." FASEB J. 5, 2093-2098 (1991).

\* cited by examiner

GENETIC POLYMORPHISMS AND INFERTILITY

RELATED APPLICATIONS

This application claims priority to U.S. Provisional Patent Application Ser. No. 61/039,217, filed Mar. 25, 2008, which is related to International Application PCT2006/038887, filed Oct. 5, 2006, which is based on and claims priority to U.S. Provisional Patent Application Ser. No. 60/723,979, filed Oct. 5, 2005, each of which is incorporated herein in its entirety.

GOVERNMENT INTEREST

This invention was made with U.S. Government support under Grant Nos. RO1 DK55865, and P30 DK56350 awarded by the National Institutes of Health. As such, the U.S. Government has certain rights in the invention.

TECHNICAL FIELD

The presently disclosed subject matter relates to methods of screening for and treating low sperm motility in male subjects. In another aspect, the presently disclosed subject matter relates to methods of screening for and treating subjects having impaired mitochondrial function as a result of a defect in one or more choline metabolism genes.

BACKGROUND

Choline is an essential nutrient, and eating a choline deficient diet results in hepatosteatosis and liver and muscle damage in humans and rodents (Buchman et al., 1995; Zeisel, 2005; Zeisel et al., 1991). In rodents, choline in maternal diet during pregnancy is important for normal fetal brain development (Albright et al., 1999a; Albright et al., 1999b; Craciunescu et al., 2003; Jones et al., 1999; Niculescu et al., 2006). Choline has three possible metabolic fates: it can be acetylated to form acetylcholine, an important neurotransmitter; it can be phosphorylated and then used as a constituent of membranes; and it can be oxidized to form betaine and then used as a methyl donor (Zeisel, 2006). Choline dehydrogenase (CHDH, EC 1.1.99.1), an inner mitochondrial membrane protein, is the enzyme responsible for catalyzing the first of two reactions leading to the production of betaine through the oxidation of dietary choline (Chi-Shui and Ru-Dan, 1986; de Ridder and van Dam, 1973; Haubrich and Gerber, 1981; Huang and Lin, 2003; Mann and Guastel, 1937; Rendina and Singer, 1959). It is through betaine that choline contributes to the pool of methyl groups available for DNA and protein methylation (Olthof and Verhoef, 2005). CHDH is primarily expressed in liver and kidney, with humans having the highest expression levels in kidney.

CHDH activity can influence tissue choline metabolite concentrations because the oxidation of choline is irreversible, committing the choline moiety to the methyl donation pathway (Zeisel 2005). Choline that is not used to form betaine can be acetylated to form acetylcholine, or phosphorylated to form phosphatidylcholine and sphingomyelin (Zeisel 2006). CHDH activity can influence tissue homocysteine concentrations because betaine donates a methyl group to homocysteine (tHcy), catalyzed by betaine:homocysteine methyl transferase (BHMT, EC 2.1.1.5). The product of this reaction is methionine which is the precursor for S-adenosylmethionine (SAM), the most important methyl donor in biochemical reactions (including DNA and protein methylations). Dietary betaine supplementation is effective in lowering plasma tHcy concentrations in humans (Olthof and Verhoef 2005); elevated plasma tHcy concentration is associated with increased risk of cardiovascular disease (Glueck, Shaw et al. 1995; Melenovsky, Stulc et al. 2003).

Some humans are more susceptible to developing organ dysfunction when fed a choline deficient diet because they have one of several single nucleotide polymorphisms (SNPs) in genes related to choline metabolism (da Costa et al., 2006). One such functionally important SNP, rs12676, is located in the coding region of the CHDH gene (da Costa et al., 2006). This is a common SNP, with 42% of the Chapel Hill, N.C., United States of America, population having at least one allele (da Costa et al., 2006). It has been reported that 83% of pre-menopausal women heterozygous for the rs12676 allele developed organ dysfunction when fed a choline deficient diet compared to only 20% of women with a wildtype genotype (da Costa et al., 2006).

In addition, it has been reported that dietary choline deficiency can alter reproductive performance in chickens and boar (Einarsson and Gustafsson, 1973; Ferguson et al., 1975). Sperm motility depends on normal mitochondrial function (Kasai T, et al., 2002). Mitochondrial membranes must maintain an electrochemical gradient in order for oxidative phosphorylation and ATP generation to proceed. According to the 2002 National Survey of Family Growth, approximately 2.1 million couples per year in the United States seek help in dealing with infertility. Of these couples, roughly 30% of the infertility can be attributed to male factor infertility. Asthenospermia, the condition of having low sperm motility, is present in 15%-17% (Maconochie et al., 2004; Thonneau et al., 1991) of these men and, in many cases, the cause is unknown.

The presently disclosed subject matter describes methods of screening for and treating low sperm motility in male subjects as a result of a defect in one or more choline metabolism genes. In another aspect, the presently disclosed subject matter describes methods of screening for and treating subjects having impaired mitochondrial function as a result of a defect in one or more choline metabolism genes.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently disclosed subject matter, a method is provided for screening for a cause of low sperm motility in a male subject, comprising, determining a genotype of a subject with respect to at least one choline metabolism gene; and comparing the genotype of the subject with at least one reference choline metabolism genotype associated with a low sperm motility, wherein a similarity in the reference and subject genotypes is indicative of a cause of low sperm motility.

In some embodiments of the presently disclosed subject matter, a method is provided for screening for defects in mitochondrial function, comprising: determining a genotype of a subject with respect to at least one choline metabolism gene; and comparing the genotype of the subject with at least one reference choline metabolism genotype associated with impaired mitochondrial function, wherein a similarity in the reference and subject genotypes indicates a defect in mitochondrial function.

In some embodiments of the presently disclosed subject matter, determining the genotype of the subject comprises: identifying at least one polymorphism of the choline metabolism gene(s); identifying at least one haplotype of the choline metabolism gene(s); identifying at least one polymorphism unique to at least one haplotype of the choline metabolism gene(s); identifying at least one polymorphism exhibiting high linkage disequilibrium to at least one polymorphism unique to the choline metabolism gene(s); identifying at least one polymorphism exhibiting high linkage disequilibrium to the choline metabolism gene(s); or combinations of parts (i)-(v).

In some embodiments of the presently disclosed subject matter, the subject is a mammal or a human. In some embodiments of the presently disclosed subject matter, the choline metabolism gene is selected from the group consisting of choline dehydrogenase (CHDH); phosphatidylethanolamine N-methyltransferase (PEMT); 5,10-methylenetetrahydrofolate dehydrogenase 1 (MTHFD1); betaine: homocysteine methyltransferase (BHMT); 5,10-methylene tetrahydrofolate reductase (MTHFR); reduced folate carrier 1 (RFC1); ATP-binding cassette, sub-family B, member 4 (ABCB4); solute carrier family 44, member 1 (SLC44A1); choline kinase alpha (CHKA); choline kinase beta (CHKB); and combinations thereof.

In some embodiments of the presently disclosed subject matter, the reference choline metabolism genotype associated with a low sperm motility comprises a CHDH genotype comprising a G432T (rs12676) polymorphism, a PEMT genotype comprising a G774C (rs12325817) polymorphism or a MTHFD1 genotype comprising a G1958A (rs2236225) polymorphism.

In some embodiments of the presently disclosed subject matter, a method is provided for treating male infertility due to low sperm motility, comprising, administering to the subject an effective amount of a choline metabolism supplement composition, wherein the choline metabolism supplement composition at least partially ameliorates the low sperm motility. In some embodiments of the presently disclosed subject matter, the choline metabolism supplement composition comprises folate or betaine. In some embodiments, the method further comprises screening for a choline metabolism genotype associated with a low sperm motility. In some embodiments, the choline metabolism genotype associated with a low sperm motility comprises a CHDH genotype comprising a G432T (rs12676) polymorphism, a PEMT genotype comprising a G774C (rs12325817) polymorphism or a MTHFD1 genotype comprising a G1958A (rs2236225) polymorphism.

In some embodiments of the presently disclosed subject matter, a method is provided for treating a subject having an impairment in mitochondrial function, comprising, administering to the subject an effective amount of a choline metabolism supplement composition, wherein the choline metabolism supplement composition at least partially ameliorates the impairment in mitochondrial function. In some embodiments of the presently disclosed subject matter, the choline metabolism supplement composition comprises folate or betaine. In some embodiments, the method further comprises screening for a choline metabolism genotype associated with an impairment in mitochondrial function. In some embodiments, the choline metabolism genotype associated with an impairment in mitochondrial function comprises a CHDH genotype comprising a G432T (rs12676) polymorphism, a PEMT genotype comprising a G774C (rs12325817) polymorphism or a MTHFD1 genotype comprising a G1958A (rs2236225) polymorphism.

In some embodiments of the presently disclosed subject matter, a method is provided for identifying polymorphisms indicative of low sperm motility and/or impaired mitochondrial function, the method comprising: identifying one or more polymorphisms of at least one choline metabolism gene of a subject that exhibits a high linkage disequilibrium to a reference choline metabolism genotype that is associated with low sperm motility and/or impaired mitochondrial function, wherein the identified polymorphism is indicative of low sperm motility and/or impaired mitochondrial function in the subject.

Accordingly, it is an object of the presently disclosed subject matter to provide methods of screening for and treating infertility due to low sperm motility. It is another object of the presently disclosed subject matter to provide methods for screening for and treating subjects having impaired mitochondrial function due to defects in choline metabolism. This and other objects are achieved in whole or in part by the presently disclosed subject matter.

An object of the presently disclosed subject matter having been stated hereinabove, other aspects and objects will become evident as the description proceeds when taken in connection with the accompanying Drawings and Examples as best described herein below.

BRIEF DESCRIPTION OF THE DRAWINGS

FIG. 3A is a diagram showing the targeting vector used to generate CHDH−/−. FIG. 3B is a Southern blot of PCR products showing the genotyping results.

FIGS. 5A and 5B are light Microscopic images of testis histology. FIGS. 5C-5F are transmission electron microscopy images of sperm. Electron microscopy of a cross section of sperm tail (FIG. 5D) shows that the mitochondria within sperm are swollen and distorted in CHDH−/− mice, but are normal in CHDH+/+ mice (FIG. 5C). Another view of these sperm tails (longitudinal section) is shown in FIGS. 5E and 5F, which show that the mitochondria are swollen and distorted in CHDH−/− mice, but are normal in CHDH+/+ mice.

FIG. 10A is a photograph showing mitochondrial morphology of sperm taken from WT (CHDH+/+) mice using a transmission electron microscope (TEM). FIG. 10B is a schematic diagram showing a normal sperm anatomy.

FIG. 16A shows the results of MTT oxidation. Mitochondria were purified from fresh liver, kidney, brain, skeletal and cardiac muscle tissues and MTT oxidation determined as described herein. Values were normalized to the amount of mitochondrial protein assayed. Results are presented as mean±SEM, *$p<0.05$, n=9-11 animals/group. Mitochondrial function as assessed by the MIT assay was abnormal in liver and kidney of CHDH−/− mice. FIG. 16B shows the results of the membrane potential assay. Mitochondria were purified from fresh liver, kidney, brain, skeletal and cardiac muscle tissues and JC-1 staining determined as described in methods. Assays were performed in duplicate and values were normalized to the amount of mitochondrial protein assayed. Results presented are as mean±SEM, n=5 animals/group. Mitochondrial function as assessed by the membrane potential assay was normal in these organs of CHDH−/− mice.

FIG. 17A shows spermatozoa concentration in million sperm per mL. Spermatozoa concentration was determined by counting cells using a hemocytometer. Results are presented as mean±SEM, n=9-11 animals per genotype. FIG. 17B shows sperm motility. Motility assays were performed by counting the number of progressively motile sperm per total number of sperm in 5 squares of a hemocytometer. The results are presented as the mean % motility±SEM, $p<0.001$, n=8-9 animals per genotype. FIG. 17C shows the results of MIT oxidation. Absorbance values were normalized to the number of sperm assayed. All assays were performed in duplicate. The value for each animal is the mean of 4 assays (2 cauda epididymii, each assayed in duplicate per animal). Results are presented as the mean±SEM, $p<0.05$, n=5 animals/group. FIG. 17D shows membrane potential. The number of cells that fluoresced red was counted in 5 random fields of vision for each sample and results are expressed as a percent of the total cells in those fields. Results are presented as mean±SEM, $p<0.001$, n=5 animals/group.

DETAILED DESCRIPTION

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Figure 1:
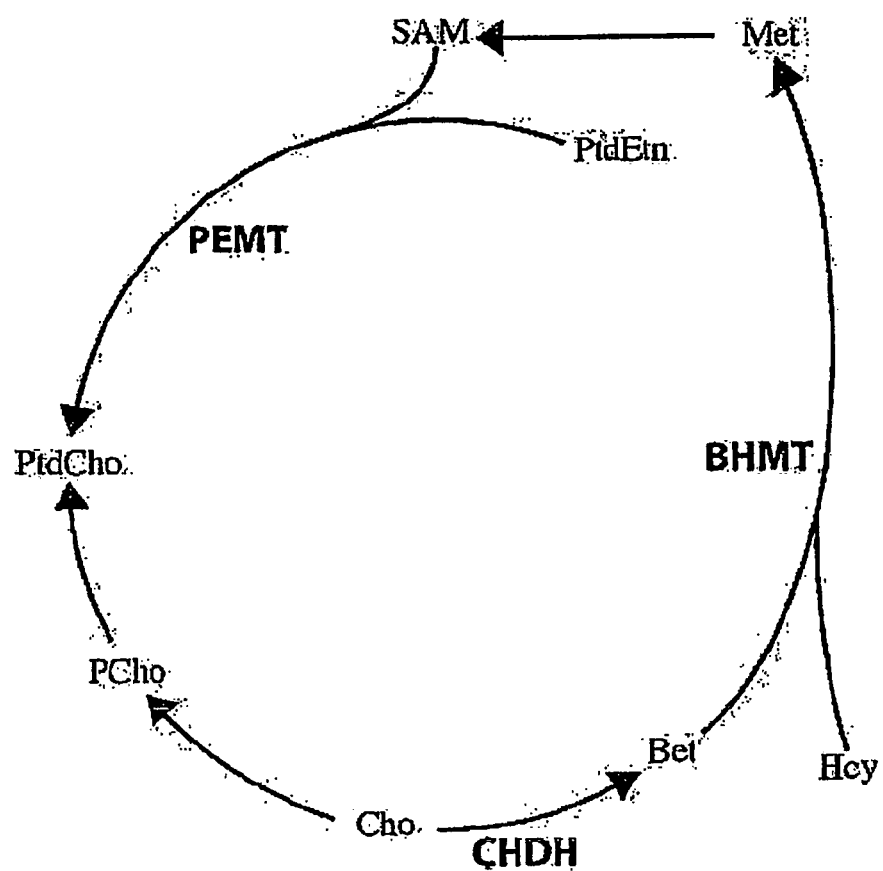
FIG. 1 is a diagram showing three genes involved in choline metabolism. PEMT=phosphatidylethanolamine N-methyltransferase, which catalyzes the reaction to make phosphatidylcholine (PtdCho) from phosphatidylethanolamine (PtdEtn) using S-adenosylmethionine (SAM) to donate methyl groups; CHDH=choline dehydrogenase, which along with betaine aldehyde dehydrogenase irreversibly oxidizes choline (Cho) to form betaine (Bet); BHMT=betaine:homocysteine methyltransferase, which donates a methyl group to homocysteine (Hcy) to form methionine (Met); PCho=phosphocholine.
Figure 2:
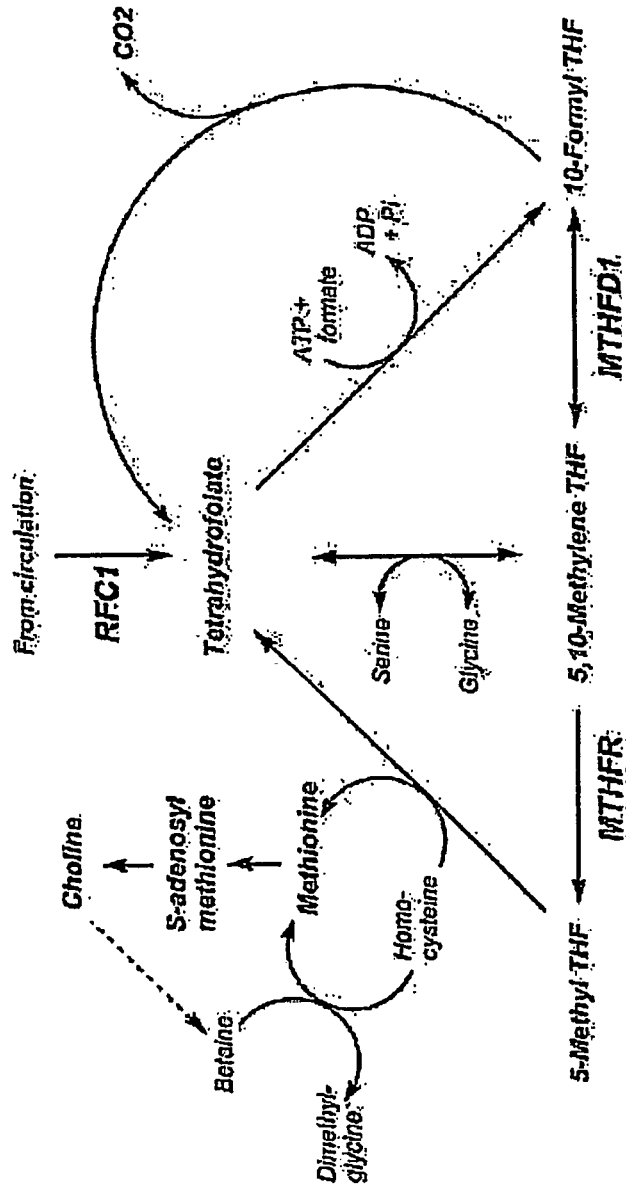
FIG. 2 is a diagram showing three polymorphic genes that are involved in folate-mediated one-carbon transfer. THF, tetrahydrofolate; MTHFR, 5,10-methylene tetrahydrofolate reductase; MTHFD1, cytosolic 5,10-methylene tetrahydrofolate dehydrogenase; and RFC1, reduced folate carrier 1.

A "choline metabolism gene" as used herein refers to a polynucleotide expressing a protein that functions, at least in part, in the metabolism of choline. "Choline metabolism" as used herein is intended to encompass all physiological aspects of choline production, function, and degradation, including but not limited to choline synthesis and catabolism, as well as choline use within other metabolic pathways, including for example the physiological utilization of choline in methyl donation reactions (e.g., folate-mediated one-carbon transfer). Choline, one-carbon and folate metabolism are interrelated and therefore, the term "choline metabolism" is intended to include one-carbon and folate metabolism as well. Exemplary non-limiting pathways of choline metabolism are shown in FIGS. 1 and 2 and each of the proteins disclosed in these pathways are specifically intended to be included within the definition of a protein that functions in the metabolism of choline (i.e., a choline metabolism protein). Thus, in some embodiments a choline metabolism gene is a polynucleotide encoding, for example, PEMT, CHDH, MTHFD1, BHMT, MTHFR, RFC1, ABCB4, SLC44A1, CHKA, or CHKB.

"PEMT gene" as used herein refers in some embodiments to a gene encoding a phosphatidylethanolamine N-methyltransferase protein (PEMT) and/or associated regulatory sequences. PEMT transfers methyl groups between molecules and can function to catalyze a reaction to produce phosphatidylcholine (PtdCho) from phosphatidylethanolamine (PtdEtn) using S-adenosylmethionine (SAM) to donate methyl groups. An exemplary PEMT gene can be a human PEMT gene located within a PEMT locus on chromosome 17 (GENBANK® Accession No. NC_000017) between about nucleotide positions 17,349,830 and 17,435,665.

"CHDH gene" as used herein refers in some embodiments to a gene encoding a choline dehydrogenase protein (CHDH) and/or associated regulatory sequences. CHDH can function to irreversibly oxidize choline to form betaine. An exemplary CHDH gene can be a human CHDH gene located within a CHDH locus on chromosome 17 (GENBANK® Accession No. NC_000003) between about nucleotide positions 53,826,844 and 53,833,075.

"MTHFD1 gene" as used herein refers in some embodiments to a gene encoding a cytosolic 5,10-methylene tetrahydrofolate dehydrogenase (MTHFD1) protein and/or associated regulatory sequences. MTHFD1 catalyzes the transfer of hydrogens from donor to acceptor molecules. MTHFD1 can catalyze the conversion of 5,10-methylene tetrahydrofolate to 10-formyl tetrahydrofolate, and vice versa. An exemplary MTHFD1 gene can be a human MTHFD1 gene located within a MTHFD1 locus on chromosome 14 (GENBANK® Accession No. NC_000014) between about nucleotide positions 63,924,899 and 63,994,774.

"BHMT" gene as used herein refers in some embodiments to a gene encoding a betaine: homocysteine methyltransferase (BHMT) protein and/or associated regulatory sequences. BHMT catalyzes the transfer of a methyl group to homocysteine from betaine to form methionine. An exemplary BHMT gene can be a human BHMT gene located within a BHMT locus on chromosome 5 (GENBANK® Accession No. NC_000005) between about nucleotide positions 78,443,465 and 78,462,695.

"MTHFR" gene as used herein refers in some embodiments to a gene encoding a 5,10-methylene tetrahydrofolate reductase (MTHFR) protein and/or associated regulatory sequences. MTHFR can catalyze the conversion of 5,10-methylene tetrahydrofolate to 5-methyl tetrahydrofolate. An exemplary MTHFR gene is a human MTHFR gene located within a MTHFR locus on chromosome 1 (GEN BANK® Accession No. NC_000001) between about nucleotide positions 11,773,324 and 11,785,760.

"RFC1" gene as used herein refers in some embodiments to a gene encoding a reduced folate carrier 1 (RFC1) protein and/or associated regulatory sequences. RFC1 can function, for example, as a folate transporter protein. An exemplary RFC1 gene is a human RFC1 gene located within a RFC1 locus on chromosome 4 (GENBANK® Accession No. NC_000004).

"ABCB4" gene as used herein refers in some embodiments to a gene encoding an ATP-binding cassette, sub-family B, member 4 (ABCB4) protein and/or associated regulatory sequences. ABCB4 is a transmembrane protein that can bind ATP and use the energy to drive the transport of various molecules across all cell membranes. An exemplary ABCB4 gene is a human ABCB4 gene located within a ABCB4 locus on chromosome 7 (GENBANK® Accession No. NC_000007) between about nucleotide positions 86,869,348 and 86,942,717.

"SLC44A1" gene as used herein refers in some embodiments to a gene encoding a solute carrier family 44, member 1 (SLC44A1) protein and/or associated regulatory sequences. SLC44A1 can transport choline molecules. An exemplary SLC44A1 gene is a human SLC44A1 gene located within a SLC44A1 locus on chromosome 9 (GENBANK® Accession No. NC_000009).

"CHKA" gene as used herein refers in some embodiments to a gene encoding a choline kinase alpha (CHKA) protein and/or associated regulatory sequences. CHKA can phosphorylate choline molecules. An exemplary CHKA gene is a human CHKA gene located within a CHKA locus on chromosome 11 (GENBANK® Accession No. NC_000011) between about nucleotide positions 67,567,632 and 67,645,220.

"CHKB" gene as used herein refers in some embodiments to a gene encoding a choline kinase beta (CHKB) protein and/or associated regulatory sequences. CHKB can phosphorylate choline molecules. An exemplary CHKB gene is a human CHKB gene located within a CHKB locus on chromosome 22 (GENBANK® Accession No. NC_000022) between about nucleotide positions 49,364,476 and 49,368,076.

As used herein, the term "expression" generally refers to the cellular processes by which an RNA is produced by RNA polymerase (RNA expression) or a polypeptide is produced from RNA (protein expression).

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

As used herein, the term "DNA segment" means a DNA molecule that has been isolated free of total genomic DNA of a particular species. Included within the term "DNA segment" are DNA segments and smaller fragments of such segments, and also recombinant vectors, including, for example, plasmids, cosmids, phages, viruses, and the like.

As used herein, the term "genotype" means the genetic makeup of an organism. Expression of a genotype can give rise to an organism's phenotype, i.e. an organism's physical traits.

"Determining the genotype" of a subject, as used herein, can refer to determining at least a portion of the genetic makeup of an organism and particularly can refer to determining a genetic variability in the subject that can be used as an indicator or predictor of phenotype. The genotype determined can be the entire genome of a subject, but far less sequence is usually required. The genotype determined can be as minimal as the determination of a single base pair, as in determining one or more polymorphisms in the subject. Further, determining a genotype can comprise determining one or more haplotypes. Still further, determining a genotype of a subject can comprise determining one or more polymorphisms exhibiting high linkage disequilibrium to at least one polymorphism or haplotype having genotypic value.

As used herein, the term "polymorphism" refers to the occurrence of two or more genetically determined alternative variant sequences (i.e., alleles) in a population. A polymorphic marker is the locus at which divergence occurs. Preferred markers have at least two alleles, each occurring at a frequency of greater than 1%. A polymorphic locus may be as small as one base pair (e.g., a single nucleotide polymorphism (SNP)). Exemplary SNPs are disclosed herein and can be referenced by accession number (e.g., "rs number"). The rs numbers (searchable through NCBI's Entrez SNP website) comprise the SNP as well as proximate contiguous nucleotides provided to place the SNP in context within the gene. Thus, rs numbers referenced herein are intended to indicate the presence of the SNP and not to require the presence of all or part of the contiguous nucleotide sequence disclosed therein. Further, reference to a particular polymorphism is intended to also encompass the complementary nucleotide(s) on the complementary nucleotide strand (e.g., coding and non-coding polynucleotides).

As used herein, "haplotype" means the collective characteristic or characteristics of a number of closely linked loci with a particular gene or group of genes, which can be inherited as a unit. For example, in some embodiments, a haplotype can comprise a group of closely related polymorphisms (e.g., single nucleotide polymorphisms (SNPs)). In some embodiments, the determined genotype of a subject can be particular haplotypes for one or more of PEMT, CHDH, BHMT, MTHFD1, MTHFR, RFC1, ABCB4, SLC44A1, CHKA, and CHKB.

As used herein, "linkage disequilibrium" (LD) means a derived statistical measure of the strength of the association or co-occurrence of two independent genetic markers. Various statistical methods are known in the art for summarizing LD between two markers.

In some embodiments, determining the genotype of a subject can comprise identifying at least one polymorphism (e.g., an SNP) of at least one gene, such as for example CHDH, PEMT, BHMT, MTHFD1, MTHFR, RFC1, ABCB4, SLC44A1, CHKA, CHKB, and combinations thereof. In some embodiments, determining the genotype of a subject can comprise identifying at least one haplotype of a gene, such as for example CHDH, PEMT, BHMT, MTHFD1, MTHFR, RFC1, ABCB4, SLC44A1, CHKA, CHKB, and combinations thereof. In some embodiments, determining the genotype of a subject can comprise identifying at least one polymorphism unique to at least one haplotype of a gene, such as for example CHDH, PEMT, BHMT, MTHFD1, MTHFR, RFC1, ABCB4, SLC44A1, CHKA, CHKB, and combinations thereof. In some embodiments, determining the genotype of a subject can comprise identifying at least one polymorphism exhibiting high linkage disequilibrium to at least one polymorphism unique to at least one haplotype, such as for example CHDH haplotype, PEMT haplotype, BHMT haplotype, MTHFD1 haplotype, MTHFR haplotype, RFC1 haplotype, ABCB4 haplotype, SLC44A1 haplotype, CHKA haplotype, CHKB haplotype, or combinations thereof. In some embodiments, determining the genotype of a subject can comprise identifying at least one polymorphism exhibiting high linkage disequilibrium to at least one haplotype, such as for example CHDH haplotype, PEMT haplotype, BHMT haplotype, MTHFD1 haplotype, MTHFR haplotype, RFC1 haplotype ABCB4 haplotype, SLC44A1 haplotype, CHKA haplotype, CHKB haplotype, or combinations thereof.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product.

"Reference genotype" as used herein refers to a previously determined pattern of genetic variation associated with a particular phenotype, such as for example male infertility due to low sperm motility and/or impaired mitochondrial function. The reference genotype can be as minimal as the determination of a single base pair, as in determining one or more polymorphisms in the subject. Further, the reference genotype can comprise one or more haplotypes. Still further, the reference genotype can comprise one or more polymorphisms exhibiting high linkage disequilibrium to at least one polymorphism or haplotype. In some particular embodiments, the reference genotype comprises one or more polymorphisms (e.g., SNPs) and/or haplotypes of CHDH, PEMT, BHMT, MTHFD1, MTHFR, RFC1, ABCB4, SLC44A1, CHKA, CHKB, or combinations thereof determined to be associated with male infertility due to low sperm motility and/or impaired mitochondrial function. In some embodiments, the haplotypes represent a particular collection of specific single nucleotide polymorphisms.

As used herein, "mitochondrial dysfunction", "impairment in mitochondrial function" and "impaired mitochondrial function" are used interchangeably and refer to a reduced level of mitochondrial function as compared to that observed in a subject having normal mitochondrial function. In some embodiments, the impaired mitochondrial function can refer to mitochondrial function in mitochondria of the liver, brain, kidney, skeletal muscle, cardiac muscle, testis or sperm. In some embodiments, the mitochondrial function in a subject with impaired mitochondrial function can be reduced by 10%, 15%, 25%, 50%, 75% or 100%, as compared to a subject with normal mitochondrial function. In some embodiments, the impaired mitochondrial function can be attributed to a genotype comprising a polymorphism, such as but not limited to a CHDH genotype comprising a G432T (rs12676) polymorphism, a PEMT genotype comprising a G774C (rs12325817) polymorphism or a MTHFD1 genotype comprising a G1958A (rs2236225) polymorphism.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. A p-value in some embodiments less than or equal to 0.05, in some embodiments less than 0.01, in some embodiments less than 0.005, and in some embodiments less than 0.001, are regarded as significant.

"Treatment" and "treating" as used herein refer to any treatment of one or more defects in choline metabolism genes and includes: (i) preventing the health effect from occurring in a subject which may be predisposed to the health effect, but has not yet been diagnosed as having it; (ii) inhibiting the health effect, i.e., arresting its further development; or (iii) relieving the health effect, i.e., causing regression of clinical symptoms of the health effect.

II. Representative Embodiments

Choline is an essential nutrient required for maintaining the integrity of cell membranes, proper cellular signaling, generation of neurotransmitters, and methylation of biological molecules. Choline is oxidized by choline dehydrogenase and betaine aldehyde dehydrogenase, resulting in formation of betaine, which adds to the methyl groups available for methylation reactions. Oxidation of choline by choline dehydrogenase is the first of two oxidations that convert choline to betaine, thereby committing the choline molecule to the methyl-donation pathway rather than to membrane synthesis.

Figure 6:
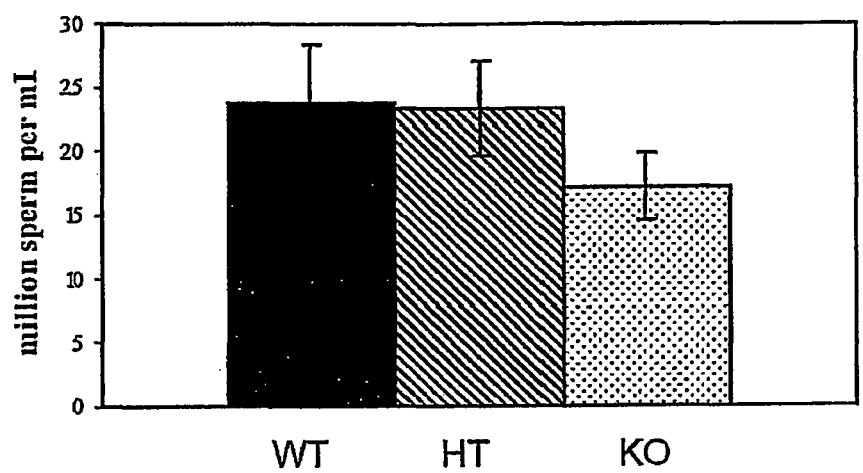
FIG. 6 is a bar graph showing mouse sperm concentration. Three different mouse genotypes are depicted: wild-type mice (WT; solid bar), mice in which one copy of the CHDH gene (CHDH+/−) has been knocked out (HT; hatched bar), and mice in which both copies of the CHDH gene (CHDH−/−) have been knocked out (KO; stippled bar). Sperm concentration was only modestly lower in CHDH−/− mice.
Figure 8:
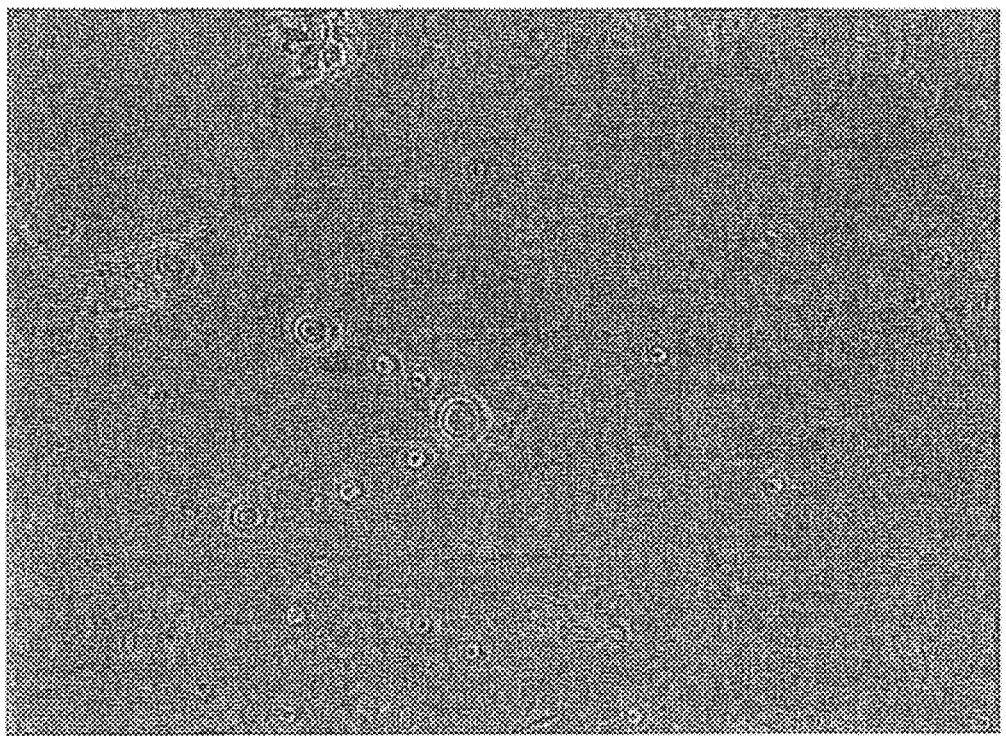
FIG. 8 is a photograph showing sperm motility of WT (CHDH+/+) mice using light microscopy.
Figure 9:
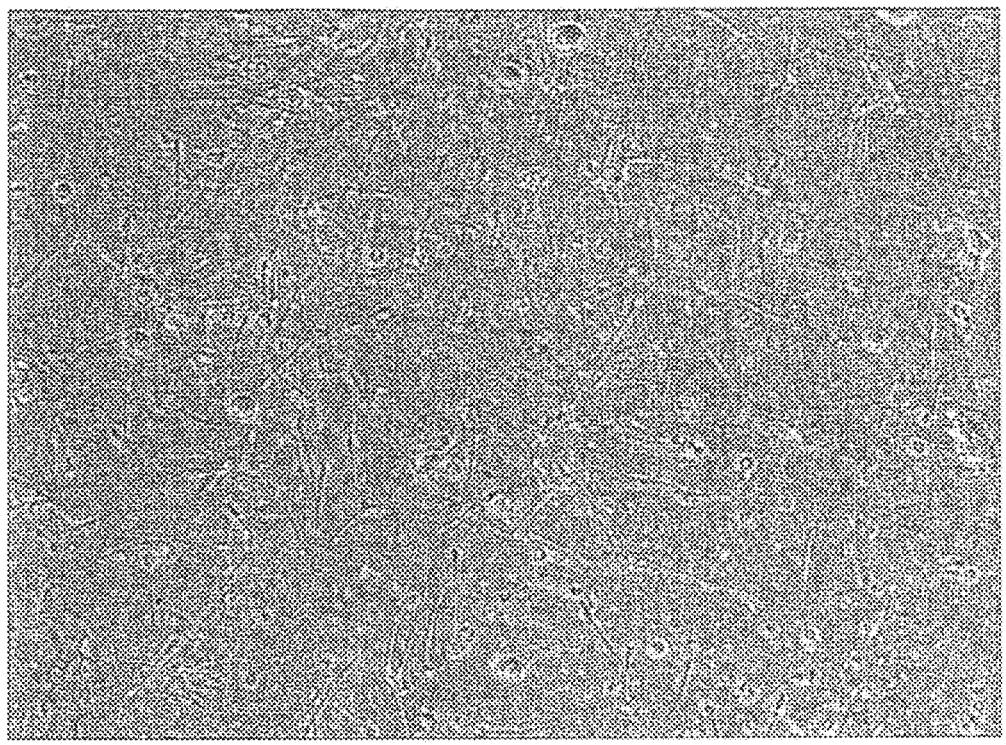
FIG. 9 is a photograph showing sperm motility of KO (CHDH−/−) mice using light microscopy.

In one aspect, the presently disclosed subject matter is related to the observation that male mice with a knock-out genotype for the choline dehydrogenase gene (CHDH−/−mice), display normal mating behavior, but are unable to reproduce (See Examples 1 & 2). Sperm concentrations for mice having a wild-type genotype (CHDH+/+), heterozygous knock-out genotype (CHDH+/−) or homozygous knock-out genotype (CHDH−/−) for the CHDH gene are shown in FIG. 6. While the sperm concentrations are not significantly different among the three genotypes, only 15% of CHDH−/− sperm are progressively motile compared to CHDH+/+ and CHDH+/− sperm which both average 58% progressive motility (see FIGS. 7, 8 & 9).

Figure 10A:
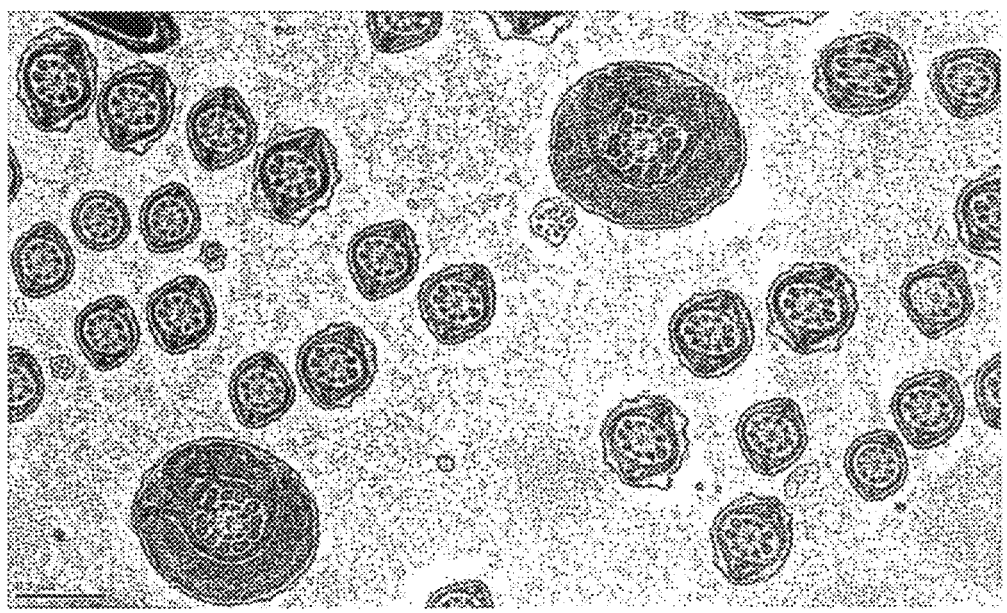
FIGS. 10A-10B depict sperm morphology.

Consistent with knocking out the choline dehydrogenase enzyme activity that catalyzes the formation of betaine, betaine levels were very low or undetectable in seminal vesicle, epididymis and testis from CHDH−/− male mice (see Example 4). In contrast, betaine levels of CHDH+/+ male mice were approximately 100-fold higher. Further, transmission electron microscopy (TEM) experiments indicate the presence of mitochondrial malformation in the sperm cells from the CHDH−/− mice (see FIGS. 10A and 11). In addition to the effects on sperm observed for the CHDH−/− mice, mice in which the choline dehydrogenase gene has been knocked out also exhibit mitochondrial defects in other tissues besides sperm, such as liver, kidney, brain, skeletal muscle and cardiac muscle (see FIGS. 12-15). Without limiting the presently disclosed subject matter to any particular mechanism of action, it is noted that betaine is a cellular osmolyte, and changes in tonicity of sperm cells as well as increases in osmolarity of spermatic fluid, can be detrimental to sperm motility. Therefore, betaine could play a role in maintaining the spermatic environment.

Accordingly, in some embodiments of the presently disclosed subject matter, methods are provided for determining a genotype of a subject with respect to a particular gene or genes having a role in choline metabolism to screen for low sperm motility and/or impaired mitochondrial function. CHDH, PEMT, BHMT, MTHFD1, MTHFR, RFC1, ABCB4, SLC44A1, CHKA, and CHKB genes encode for proteins that can each, and in combination with one another, play a role in choline metabolism and individual sensitivity to choline deficiency. In particular, for example, SNPs in the choline dehydrogenase (CHDH) and phosphatidylethanolamine N-methyltransferase (PEMT) genes are common and have been shown to affect dietary requirements for the nutrient choline and to indicate susceptibility to developing organ dysfunction on a low choline diet. As described herein above, mice in which the choline dehydrogenase gene has been knocked out exhibit infertility, low sperm motility, and impaired mitochondrial function relative to their wildtype counterparts.

Accordingly, in one aspect of the presently disclosed subject matter, a method is provided for screening for the presence of low sperm motility in a male subject, comprising, determining a genotype of the subject with respect to at least one choline metabolism gene; and comparing the genotype of the subject with at least one reference choline metabolism genotype associated with a low sperm motility, wherein a similarity in the reference and subject genotypes indicates low sperm motility.

In another aspect of the presently disclosed subject matter, a method is provided for screening for impaired mitochondrial function, comprising, determining a genotype of a subject with respect to at least one choline metabolism gene; and comparing the genotype of the subject with at least one reference choline metabolism genotype associated with a defect in mitochondrial function, wherein a similarity in the reference and subject genotypes indicates a defect in mitochondrial function. In some embodiments, the mitochondrial dysfunction can be in mitochondria of liver, kidney, brain, skeletal muscle, cardiac muscle, or sperm.

In some embodiments of the presently disclosed subject matter, methods are provided for determining the genotype of the subject with respect to the at least one choline metabolism gene, such as for example but not limited to CHDH, PEMT, BHMT, MTHFD1, MTHFR, RFC1, ABCB4, SLC44A1, CHKA, CHKB, and combinations thereof; and comparing the genotype of the subject with at least one reference choline metabolism genotype associated with low sperm motility and/or impaired mitochondrial function, wherein a similarity in the reference and subject genotypes indicates low sperm motility and/or impaired mitochondrial function.

In some embodiments of the presently disclosed subject matter, determining the genotype of the subject with respect to one or more genes having a role in choline metabolism can comprise, identifying at least one polymorphism of the choline metabolism gene; identifying at least one haplotype of the choline metabolism gene; identifying at least one polymorphism unique to at least one haplotype of the choline metabolism gene; identifying at least one polymorphism exhibiting high linkage disequilibrium to at least one polymorphism unique to the choline metabolism gene; identifying at least one polymorphism exhibiting high linkage disequilibrium to the choline metabolism gene; or any and all combinations of the foregoing.

In some embodiments, the reference choline metabolism genotype comprises a human CHDH genotype comprising a G432T (rs12676) polymorphism (i.e., a T is present at nucleotide +432 (coding region)), a human PEMT genotype comprising a G774C (rs12325817) polymorphism (i.e., a C is present at nucleotide −774 (non-coding region)), and a human MTHFD1 genotype comprising a G1958A (rs2236225) polymorphism (i.e., an A is present at nucleotide +1958 (coding region); note "G1958A" throughout the present disclosure references the polymorphism on the minus strand, whereas the rs number discloses the complementary strand and references the polymorphism as a UT polymorphism).

Accordingly, in some embodiments, the genotype of the subject is determined and then compared to one or more reference genotypes associated with low sperm motility and/or impaired mitochondrial function and if the determined subject genotype matches the reference genotype, the subject is indicated as having low sperm motility and/or impaired mitochondrial function.

In addition, a genotype of a subject need not necessarily be determined based on a need to compare the subject's genotype to a reference genotype. Instead, for example, one or more polymorphisms exhibiting high linkage disequilibrium to a reference genotype associated with low sperm motility and/or impaired mitochondrial function can be identified. Such polymorphisms exhibiting high linkage disequilibrium can be equally predictive of low sperm motility and/or impaired mitochondrial function. In some embodiments, the reference genotype associated with low sperm motility and/or impaired mitochondrial function can be, for example, a CHDH, PEMT, BHMT, MTHFD1, MTHFR, RFC1, ABCB4, SLC44A1, CHKA, or CHKB polymorphism or haplotype, or combinations thereof.

For example, there are at least 98 known SNPs for PEMT (Saito et al. (2001)). Using techniques known in the art, one or more of these SNPs can be selected based on whether the SNP exhibits high linkage disequilibrium to one or more of the SNPs of the reference PEMT genotypes. Thus, after a review of the guidance provided herein, one of ordinary skill would appreciate that any one or more polymorphisms exhibiting high linkage disequilibrium to a polymorphism or haplotype of a reference PEMT genotype could likewise be effective as a genotypic indicator of low sperm motility and/or impaired mitochondrial function. In a similar manner, polymorphisms exhibiting high linkage disequilibrium to other choline metabolism genes including CHDH, BHMT, MTHFD1, MTHFR, RFC1, ABCB4, SLC44A1, CHKA, and CHKB could also be identified as being useful genotypic indicators of low sperm motility and/or impaired mitochondrial function.

In another aspect, the presently disclosed subject matter provides a method for treating male infertility due to low sperm motility, comprising, administering to the subject an effective amount of a choline metabolism supplement composition, wherein the choline metabolism supplement composition at least partially ameliorates the low sperm motility. In some embodiments of the presently disclosed methods, the choline metabolism supplement composition comprises folate or betaine. Indeed, betaine is available as a human diet supplement.

In another aspect of the presently described subject matter, a method is provided for treating a subject having impaired mitochondrial function, comprising, administering to the subject an effective amount of a choline metabolism supplement composition, wherein the choline metabolism supplement composition at least partially ameliorates the impairment in mitochondrial function. In some embodiments, the choline metabolism supplement composition comprises folate or betaine. In some embodiments, the mitochondrial function ameliorated by choline metabolism supplementation can comprise mitochondria of liver, kidney, brain, skeletal muscle, cardiac muscle or sperm. In some embodiments, the impaired mitochondrial function can result in abnormal muscle function. In some embodiments, administering an effective amount of choline metabolism supplement composition at least partially ameliorates the impairment in muscle mitochondrial function and thereby at least partially ameliorates or treats any associated abnormal muscle function.

In addition, as the choline metabolism genes listed above have many more polymorphisms than have been specifically tested, unmeasured but causal genetic variation can be in linkage disequilibrium with the exemplary SNPs specifically genotyped. As such, the presently disclosed subject matter is intended to be inclusive of all choline metabolism gene polymorphisms correlated with choline deficiency-associated low sperm motility and defects in mitochondrial function, including those in linkage disequilibrium with polymorphisms exhibiting direct effects on choline metabolism polypeptide function. In some embodiments, screening for choline metabolism gene polymorphisms disclosed herein or known to one of ordinary skill in the art can provide for the identification of subjects with choline deficiency-associated mitochondrial function resulting in abnormal muscle function.

III. Subjects

A "subject" as the term is used herein generally refers to an animal. In some embodiments, an animal subject is a vertebrate subject. Further, in some embodiments, a vertebrate is warm-blooded and a representative warm-blooded vertebrate is a mammal. A representative mammal is most preferably a human. However, as used herein, the term "subject" includes both human and animal subjects. Thus, veterinary therapeutic uses are provided in accordance with the presently disclosed subject matter.

As such, the presently disclosed subject matter provides for the analysis and treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. A "subject" as the term is used herein can further include birds, such as for example those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, "subject" further includes livestock, including, but not limited to, domesticated swine, ruminants, ungulates, horses (including race horses), poultry, and the like.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Generation of CHDH$^{-/-}$ Mice

Methods:

All chemicals and cell media were purchased from Sigma Aldrich (St. Louis, Mo., United States of America) unless otherwise stated.

Figure 3:
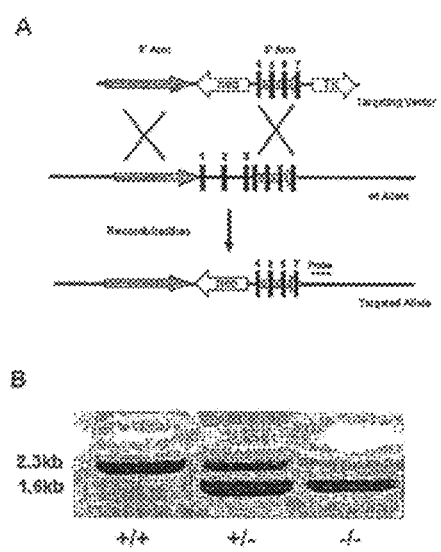
FIGS. 3A and 3B illustrate the generation of CHDH−/− mice.

To create a mouse line with a null mutation in the CHDH gene, a gene targeting vector was constructed that removed exons 1 through 3 of the gene. The 5' arm of homology was derived from the region of the gene immediately 5' of exon 1 (approximately 5.5 kb) and the 3' arm was derived from the region 3' of exon 3 (approximately 1.5 kb) and encompassed exons 4 through 7 (FIG. 3A). The vector contained positive and negative selection cassettes (neo and TK, respectively). The vector was electroporated into the mouse ES line E14TG2a. PCR-positive clones were confirmed for homologous recombination by Southern hybridization using an external probe. Targeted cells were injected into blastocysts derived from mouse strain C57Bl/6 to create transmitting chimeras.

CHDH$^{+/-}$ breeding pairs were used to generate litters comprised of CHDH$^{+/+}$, CHDH$^{+/-}$ and CHDH$^{-/-}$ mice, which were used in these experiments. Mice were maintained on AIN-76A diet containing 1.1 g/kg choline chloride (Dyets, Bethlehem, Pa., United States of America). Animals were genotyped by multiplexing PCR using TaKaRa Ex Taq DNA polymerase (TaKaRa Bio USA, Madison, Wis., United States of America) and the following primer sequences: CHDH+/+ 5'-AGGGCCACAAGTGTGGGCTGGCTGAAACTG-3' (SEQ ID NO: 1), CHDH common 5'-GCTAGCTTGAAC-CCTTTGAAGGGTCTTCTCAGACTC-3' (SEQ ID NO: 2) and CHDH neo 5'-ACGCGTCACCTTAATATGC-3' (SEQ ID NO: 3). The thermocycler program was 95° C. for 3 minutes, 94° C. for 30 seconds, 56° C. for 30 seconds, 72° C. for 3 minutes (repeated 35 times), and 72° C. for 10 minutes. CHDH$^{+/+}$ reactions produced a product 2.3 kb in size. The CHDH neo product was 1.6 kb in size (FIG. 3B). All experimental protocols were approved by the Institutional Animal Care and Use Committee (IACUC) of the University of North Carolina, Chapel Hill, N.C., United States of America.

Example 2

Characterization of CHDH$^{-/-}$ Mice

The body length and total body weight of CHDH$^{+/+}$, CHDH$^{+/-}$ and CHDH$^{-/-}$ mice from Example 1 were measured at weaning (postnatal day 21; P21), P42 and P63. The mice were weighed on a scale and a ruler was used to measure body length. "Body length" is the distance between the tip of the nose to the end of the buttock when the mouse is lying on its stomach. The genotype distribution of litters was measured by tracking the genotype results of litters produced by 20 CHDH$^{-/-}$ mating pairs over a 3-year period. A set of 10 CHDH$^{-/-}$ mice was maintained over time to determine whether or not CHDH mutation affected the survival rates of these mice. Several gender-specific phenotypes were observed to be associated with mutation, the most striking being severe asthenspermia and mitochondrial dysfunction in sperm of male CHDH$^{-/-}$ mice.

The genotype distribution for litters born to CHDH$^{+/-}$ mating pairs (604 pups total) was 137 (23%) CHDH$^{+/+}$, 303 (51%) CHDH$^{+/-}$ and 164 (27%) CHDH$^{-/-}$. Litter size for CHDH$^{+/-}$ mated pairs was 6-11 pups. Wildtype C57 mating pairs typically produce litters of 6-8. Mating a CHDH$^{-/-}$ female with a male CHDH$^{+/-}$ mouse resulted in normal size litters (6-9 pups), however mating a CHDH$^{-/-}$ male with a female CHDH$^{+/-}$ mouse resulted in no or greatly reduced size litters (one of eleven such pairs had a litter of 2 pups, both of which showed impaired growth).

There were no differences in growth among CHDH$^{+/+}$, CHDH$^{+/-}$ and CHDH$^{-/-}$ animals either in terms of body length or total body weight CHDH$^{-/-}$ mice lived for at least one year without any obvious serious health problems.

Example 3

CHDH Assay Analysis of CHDH$^{-/-}$ Mice

CHDH$^{+/+}$ and CHDH$^{-/-}$ mice were anesthetized with Halothane (Henry Schein, Inc., Melville, N.Y., United States of America). Tissues were harvested from animals and immediately snap frozen in liquid nitrogen. Liver, kidney, testis, brain and muscle were then pulverized in liquid nitrogen and stored at −80° C. until CHDH activity was assayed. Approximately 200 mg of tissue was homogenized in 500 µL cold homogenization buffer (250 mM sucrose, 50 mM Tris, 0.1 mM EDTA, pH 7.8) with a motorized tissue homogenizer. Protein concentrations were measured by Lowry assay (Lowry et al., 1951).

Enzyme activity was assessed in 50 mM sodium phosphate, 50 mM Tris base, 0.1 mM calcium chloride, 1.0 mM phenazine methosulfate (PMS), 0.15 mM unlabeled choline chloride, 0.37 µCi $^{14}$C-choline chloride (NEN-Perkin Elmer, Waltham, Mass., United States of America), and 1.5 mg of tissue homogenate. The final reaction volume was 150 uL. Reactions were assembled on ice, and then incubated at 37° C. for 40 minutes. The reactions were stopped with 15 µL 1.2N HCl. Choline and betaine were extracted from the tissue using 450 µL of methanol:chloroform (1:2). Samples were subjected to centrifugation at 300×g (1800 rpm) for 10 minutes at room temperature. 50 µL of the aqueous layer was combined with 100 µL 100% methanol and 50 of this mixture was injected onto a Pecosphere Silica column (3 uM, 4.6×83 mm) (Perkin Elmer, Norwalk, Conn., United States of America) with a Pelliguard LC-Si guard column (Supleco, Bellefonte, Pa., United States of America) for analysis by high performance liquid chromatography (Varian ProStar solvent delivery system (PS-210, Varian Inc., Palo Alto, Calif., United States of America) with a Berthold LB506 C-1 radiodetector (Oak Ridge, Tenn., United States of America)) as described previously (Pomfret et al., 1989).

In wildtype mice, kidney, liver and testis had the highest activity of CHDH, with almost no activity detected in brain and skeletal muscle; CHDH activity was undetected in cardiac muscle. Reduced CHDH activity was detected in tissues of CHDH$^{-/-}$ mice compared to CHDH$^{+/+}$ mice (Table 1). Liver samples from CHDH$^{+/-}$ mice had 37% of the CHDH activity measured in CHDH$^{+/+}$ samples.

TABLE 1

Choline Dehydrogenase (CHDH) Activity

| | pmol betaine/mg protein/min | |
|---|---|---|
| | CHDH$^{+/+}$ | CHDH$^{-/-}$ |
| Liver | 29.6 ± 2.5 | 1.0 ± 0.25*** |
| Kidney | 83.3 ± 6.8 | 0.4 ± 0.2*** |
| Brain | 0.85 ± 0.3 | 1.05 ± 0.4 |
| Muscle | 0.3 ± 0.1 | 0.1 ± 0.1 |
| Testis | 11.9 ± 1.3 | 2.2 ± 1.0*** |

Example 4

Assay for Choline Metabolites in Whole Tissues and Isolated Mitochondria in CHDH$^{-/-}$ Mice 7-week-old CHDH$^{+/+}$ and CHDH$^{-/-}$ mice were anesthetized with Halothane (Henry Schein, Inc, Melville, N.Y., United States of America) and liver, brain, kidney and testis tissues were collected. The tissues were quick frozen in liquid nitrogen and then pulverized under liquid nitrogen using a mortar and pestle.

Mitochondria from fresh liver, kidney, brain and testis were isolated using a PERCOLL® (Sigma, St. Louis, Mo., United States of America) gradient following previously described methods with some modification (Cohen and Kesler, 1999;

Shimizu et al., 2001; Cipolat et al., 2007). All buffers were ice cold and samples were kept on ice throughout the isolation procedure. Liver, kidney, brain and testis tissue was harvested from the animal and immediately placed in mitochondrial isolation buffer (MIB; 225 mM mannitol, 75 mM sucrose, 1.0 mM EGTA in 5 mM MOPS, pH 7.4). The tissue was homogenized on ice using a motorized TEFLON® pestle and glass homogenizer. Following homogenization, an equal volume of 26% PERCOLL® gradient in MIB was added to each sample to a final concentration of 13% PERCOLL® gradient. Samples were layered onto a 40%/26% PERCOLL® gradient and subjected to centrifugation at 28,000×g at 4° C. for 15 minutes using a Beckman L8-M ultracentrifuge and 70i.TI rotor. The fraction located at the interphase of the 40% and 26% PERCOLL® layers was collected, washed with MIB and pelleted by centrifugation at 7,000×g for 10 minutes at 4° C. Mitochondria pellets were resuspended in 1 mL MIB, transferred to 1.5 mL microfuge tubes and centrifuged at 11,000×g for 10 minutes at 4° C. The resulting mitochondrial pellet was resuspended in MIB containing 10% 10 mg/mL bovine serum albumin (BSA).

Skeletal muscle (vastus medialis) and cardiac muscle were harvested from mice, minced and incubated on ice in muscle extraction buffer (MEB; 110 mM KCl, 1 mM EGTA in 20 mM MOPS, pH 7.5) containing Proteinase K at a final concentration of 0.25 mg/mL for 3 minutes. Samples were pelleted and resuspended in fresh MEB plus Proteinase K and incubated on ice for 20 minutes. The Proteinase K reaction was quenched with BSA (final concentration of 10 mg/mL). Samples were pelleted washed and resuspended in 2 mL MEB and homogenized using a TEKMARO Tissumizer (Cincinnati, Ohio). Samples were subjected to centrifugation at 600×g for 5 minutes, the supernatant was transferred to a clean microfuge tube and samples were again subjected to centrifugation at 11,000×g for 10 minutes. The resulting mitochondrial pellet was resuspended in MIB plus BSA as described for liver, kidney and brain mitochondrial pellets. As with the other tissues, all procedures for muscle mitochondria isolation were performed at 4° C.

The concentration of choline metabolites in these tissues was measured using liquid chromatography-electrospray ionization-isotope dilution mass spectrometry (LC-ESI-IDMS) (Koc et al., 2002). Briefly, deuterium-labeled internal standards of choline, betaine, glycerophosphocholine (GPCho), phosphocholine (PCho), sphingomylein (SM), phosphatidylcholine (PtdCho) and 800 µl of methanol/chloroform (2:1, v/v) were added to the tissue. Samples were vortexed vigorously and incubated at −20° C. overnight. Samples were then subjected to centrifugation at 16,000×g for 5 minutes at room temperature. The supernatant was transferred to a new tube and the residue was re-extracted with 500 µl of methanol/chloroform/water (2:1:0.8, by volume). The supernatants from both extractions were combined. To the combined solution, 200 µL of chloroform, then 200 µL of water, were added to form two phases. After centrifugation at 16,000×g for 5 minutes, the aqueous phase (which contained choline) was separated from the chloroform phase (which contained PtdCho and SM). A 20 µL aliquot of the organic phase was analyzed by LC-ESI-IDMS after 20-fold dilution with methanol. The aqueous phase was dried by vacuum centrifugation (Speed-Vac; Savant Instruments, Farmingdale, N.Y., United States of America) and redissolved in 30 µL of water. After the addition of 300 µL of methanol, the aqueous phase was stored in −20° C. for 3 hours and then subjected to centrifugation at 16,000×g at 4° C. for 15 minutes to remove the precipitated compounds from the solution. A 10 µL aliquot of this solution was then analyzed by LC-ESI-IDMS.

$CHDH^{-/-}$ mice had greatly diminished hepatic betaine concentrations as compared to $CHDH^{+/+}$ mice ($p<0.001$), while having 113% higher hepatic choline concentrations ($p<0.01$) (Table 2). Hepatic phosphatidylcholine (PtdCho) concentrations were decreased in $CHDH^{-/-}$ mice, but this was a gender-specific effect. There were no differences in hepatic PtdCho between male $CHDH^{+/+}$ and $CHDH^{-/-}$ mice; however, female $CHDH^{-/-}$ mice had significantly less hepatic PtdCho (17,226±86 nmol/g) then did their female $CHDH^{+/+}$ littermates (20,108±540 nmol/g, $p<0.05$; n=6/group). $CHDH^{-/-}$ mice had significantly lower hepatic sphingomyelin (SM) concentrations compared to $CHDH^{+/+}$ mice ($p<0.05$). This change was not gender-specific. There were no genotype-related changes in hepatic glycerophosphocholine (GPCho) or phosphocholine (PCho) concentrations.

$CHDH^{-/-}$ mice had greatly diminished renal betaine concentrations as compared to $CHDH^{+/+}$ mice ($p<0.001$), increased renal choline concentrations ($p<0.05$) and more then twice as much renal PCho ($p<0.0005$) as did $CHDH^{+/+}$ littermates. There were no changes in renal GPCho or SM concentrations. While there were no significant differences in PtdCho concentrations between $CHDH^{+/+}$ and $CHDH^{-/-}$ mice compared grouped or by gender, male $CHDH^{+/+}$ animals had significantly higher renal PtdCho concentrations (25983±1558 nmol/g) than did $CHDH^{+/+}$ females (13276±1102 nmol/g; $p<0.001$, n=9/group).

TABLE 2

Choline Metabolites in Liver, Kidney, Brain and Testis Whole Tissue
nmol/g

| | | Betaine | Choline | GPCho | PCho | PtdCho | SM |
|---|---|---|---|---|---|---|---|
| Liver | $CHDH^{+/+}$ | 358 ± 37 | 202 ± 54 | 741 ± 196 | 248 ± 68 | 19226 ± 337 | 1404 ± 85 |
| | $CHDH^{-/-}$ | 56 ± 23*** | 432 ± 82** | 664 ± 124 | 305 ± 70 | 17913 ± 376* | 1082 ± 39* |
| Kidney | $CHDH^{+/+}$ | 1388 ± 207 | 3028 ± 184 | 11608 ± 2196 | 615 ± 60 | 17512 ± 2283 | 4590 ± 339 |
| | $CHDH^{-/-}$ | 25 ± 8*** | 4226 ± 389* | 8214 ± 1440 | 1221 ± 46*** | 18068 ± 1358 | 4250 ± 449 |
| Brain | $CHDH^{+/+}$ | 20 ± 5 | 238 ± 20 | 781 ± 30 | 361 ± 21 | 22322 ± 951 | 2714 ± 90 |
| | $CHDH^{-/-}$ | 10 ± 3 | 208 ± 11 | 794 ± 26 | 437 ± 14** | 22518 ± 692 | 2870 ± 47 |
| Testis | $CHDH^{+/+}$ | 4589 ± 401 | 367 ± 30 | 816 ± 45 | 4030 ± 111 | 9176 ± 773 | 1633 ± 172 |
| | $CHDH^{-/-}$ | 31 ± 11*** | 722 ± 32*** | 736 ± 26 | 4861 ± 229* | 9599 ± 819 | 1634 ± 137 |

In brain, betaine concentrations were very low in both wildtype and knockout mice. Brain PCho concentrations were increased in $CHDH^{-/-}$ mice ($p<0.05$) compared to $CHDH^{+/+}$ littermates. Brain choline, PtdCho, SM and GPCho concentrations were not different between groups.

In skeletal muscle, $CHDH^{-/-}$ animals had 1% ($p<0.001$) of the amount of betaine and 369% ($p<0.001$) of the amount of choline found in $CHDH^{+/+}$ animals. PCho concentrations were significantly increased in $CHDH^{-/-}$ skeletal muscle tissue (p<0.01). There were no changes in GPCho, PtdCho or SM concentrations.

Betaine concentrations in $CHDH^{-/-}$ heart tissue were significantly lower than $CHDH^{+/+}$ heart tissue (p<0.001) and choline concentrations significantly higher (p<0.01). No changes were measured in GPCho, PCho, PtdCho, or SM in this tissue.

Male $CHDH^{-/-}$ mice had greatly diminished testicular betaine concentrations as compared to male $CHDH^{+/+}$ mice (p<0.001). Also, they had nearly twice as much testicular choline (p<0.001) and increased testicular PCho concentrations (p<0.05). There were no changes in testicular GPCho, PtdCho or SM concentrations.

Betaine concentrations were undetectable in mitochondria purified from liver, kidney, brain, skeletal muscle, cardiac muscle and testis of $CHDH^{-/-}$ mice, while there were millimolar concentrations of betaine in mitochondria from liver, kidney, cardiac muscle and testis of $CHDH^{+/+}$ mice (Table 3). Betaine was not detected in mitochondria from brain and skeletal muscle of $CHDH^{+/+}$ mice. Choline concentrations were significantly increased in isolated mitochondria from liver (p<0.05) and kidney (p<0.001) and testis in $CHDH^{-/-}$ animals compared to $CHDH^{+/+}$ mice. There were no changes choline concentrations in brain, skeletal or cardiac muscle mitochondria due to genotype. Additionally, no changes due to genotype were noted in any tissues for GPCho, PCho, PtdCho or SM concentrations.

was increased from approximately 20% in unsupplemented CHDH−/− mice to approximately 30% in betaine supplemented CHDH−/− mice. Sperm motility in CHDH+/− mice was unaffected by betaine supplementation.

In liver a sexually dimorphic effect was observed in $CHDH^{-/-}$ mice. By 7 weeks of age, the female $CHDH^{-/-}$ mice had developed hepatosteatosis. This was not observed in the male mice. Male $CHDH^{+/+}$ and $CHDH^{-/-}$ mice do not have differences in PtdCho concentrations while a significant reduction was observed in female CHDH−/− mice. It is possible that this difference is the mechanism causing the fatty liver in females. Hepatosteatosis is a well described effect of choline deficiency, where the secretion of triglyceride from the liver as Very Low Density Lipoprotein (VLDL) requires the synthesis of a new PtdCho molecule (Yao and Vance, 1988) It is unclear why females and not males had lower PtdCho concentrations with the gene deletion.

Example 5

Tissue Histology Analysis of $CHDH^{-/-}$ Mice 7-week-old $CHDH^{+/+}$ and $CHDH^{-/-}$ mice were anesthetized with Halothane (Henry Schein, Inc, Melville, N.Y., United States of America) and whole brain, liver, kidney and vastus medialis skeletal muscle were collected. The tissues were fixed in 4% paraformaldehyde/0.2% gluteraldehyde for 72 hours, processed, paraffin embedded and sectioned for hemotoxylin and eosin staining using standard techniques.

TABLE 3

Choline Metabolites in Purified Mitochondria from Liver, Kidney, Brain, Skeletal and Cardiac Muscle umol/g

| | | Betaine | Choline | GPCho | PCho | PtdCho | SM |
|---|---|---|---|---|---|---|---|
| Liver | $CHDH^{+/+}$ | 20 ± 6 | 0.9 ± 0.3 | 49 ± 37.3 | 13.8 ± 9.4 | 204 ± 30 | 8.9 ± 1.3 |
| | $CHDH^{-/-}$ | ND* | 3.9 ± 0.9* | 29.8 ± 13 | 5.7 ± 1.3 | 178.4 ± 42.4 | 7.6 ± 2.1 |
| Kidney | $CHDH^{+/+}$ | 25.7 ± 4.5 | 0.6 ± 0.4 | 40 ± 17.5 | 2.2 ± 1.3 | 269.7 ± 34.3 | 11.3 ± 2.4 |
| | $CHDH^{-/-}$ | ND** | 21.1 ± 2.3*** | 40.2 ± 2.9 | 0.8 ± 0.2 | 221.7 ± 7.3 | 11.1 ± 1.0 |
| Brain | $CHDH^{+/+}$ | ND | 3.5 ± 1.6 | 22.9 ± 12.1 | 4.4 ± 2.2 | 327.1 ± 74 | 8.6 ± 3.1 |
| | $CHDH^{-/-}$ | ND | 3.9 ± 1.7 | 9.7 ± 1.6 | 3.9 ± 1.0 | 211 ± 23.8 | 3.2 ± 1.1 |
| Skeletal Muscle | $CHDH^{+/+}$ | ND | 2.5 ± 1.0 | 4.3 ± 2.1 | 2.2 ± 1.0 | 102.9 ± 39.4 | 4.9 ± 1.1 |
| | $CHDH^{-/-}$ | ND | 1.1 ± 0.3 | 3.8 ± 1.9 | 1.2 ± 0.5 | 68.5 ± 10 | 3.2 ± 0.4 |
| Cardiac Muscle | $CHDH^{+/+}$ | 6.5 ± 10.7 | 9.6 ± 2.0 | 27.8 ± 36.7 | 1.9 ± 1.2 | 172.4 ± 13 | 16.2 ± 1.5 |
| | $CHDH^{-/-}$ | ND | 6.3 ± 2.0 | 16.1 ± 16.6 | 0.8 ± 0.5 | 166.9 ± 31.5 | 12.6 ± 2.6 |

Deletion of CHDH resulted in a significant increase in plasma total homocysteine (tHcy) concentrations (Table 4). There was no gender-effect. There were no changes in hepatic SAM or S-adenosylhomocysteine concentrations (Table 4).

TABLE 4

Hepatic SAM/SAH and Plasma tHcy Concentrations

| | | $CHDH^{+/+}$ | $CHDH^{-/-}$ |
|---|---|---|---|
| SAM (pmol/50 mg liver tissue) | All Mice | 73.3 ± 6.2 | 57.8 ± 5.4 |
| | Males | 81.7 ± 11.1 | 61.4 ± 9.5 |
| | Females | 64.9 ± 1.7 | 54.2 ± 6.5 |
| SAH (pmol/50 mg liver tissue) | All Mice | 51.3 ± 6.7 | 53.9 ± 11.7 |
| | Males | 59.0 ± 10.3 | 59.8 ± 19.6 |
| | Females | 43.5 ± 6.9 | 44.6 ± 14.4 |
| tHcy (μM in plasma) | All Mice | 6.0 ± 0.9 | 8.6 ± 1.6 |
| | Males | 4.4 ± 0.5 | 6.7 ± 0.4* |
| | Females | 7.3 ± 1.4 | 10.2 ± 3.0 |

Figure 17:
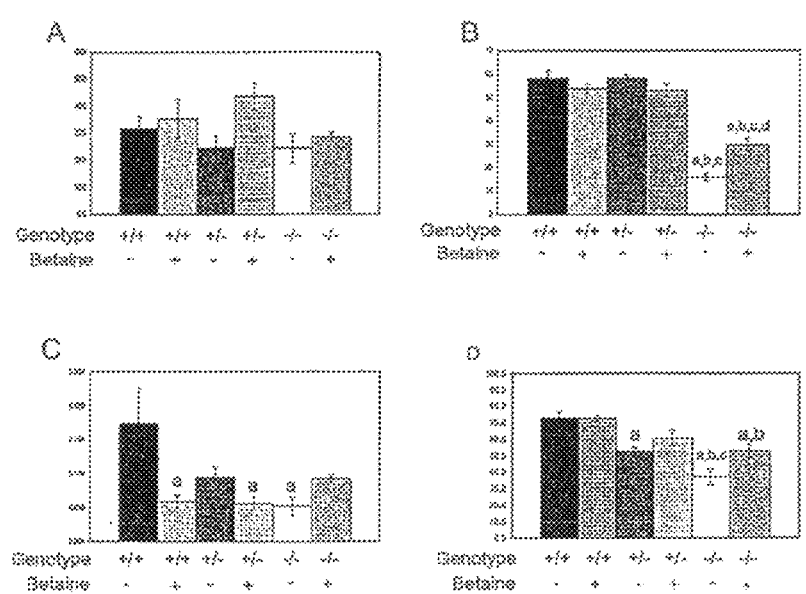
FIGS. 17A-17D are bar graphs showing the results of betaine supplementation on sperm concentration, motility and mitochondrial function in CHDH+/+ (WT), CHDH+/−, and CHDH−/− (KO) mice.

It was found that sperm motility can be at least partially restored in CHDH−/− mice given drinking water supplemented to 2% betaine for 38 days (FIG. 17B). Sperm motility Reproductive organs from adult (14 and 17 week old) $CHDH^{+/+}$ and $CHDH^{-/-}$ male mice were fixed for 24 hours in modified Davidson's fixative (11.1% formaldehyde, 15% ethanol, 5% glacial acetic acid in water). Testis and epididymal sections were stained with hemotoxylin and eosin as well as with periodic acid Schiff stain (PAS) for histological analysis. Brain sections were stained with Luxol blue. All tissues except brain were examined by a University of North Carolina at Chapel Hill Department of Laboratory Animal Medicine veterinary pathologist. Brain sections were examined by a board-certified practitioner.

Histological analysis was also used to determine if $CHDH^{-/-}$ animals had more hepatic lipid accumulation when compared to their $CHDH^{+/+}$ littermates. After anesthetizing $CHDH^{+/+}$ and $CHDH^{-/-}$ animals as described above, liver was collected and one lobe was fixed in 4% paraformaldehyde/0.2% gluteraldehyde for 24 hours. Tissue was processed and embedded according to standard techniques. 5 μm sections were stained with hematoxylin and eosin. The remaining tissue was snap frozen in liquid nitrogen and stored at −80° C. until further use. 20× images of the tissue were taken so that one portal vein was visible. Images were then coded and scored blindly by 3 laboratory members using a relative rating scale (0-4, least to most fat accumulation) developed for this experiment.

Figure 4:
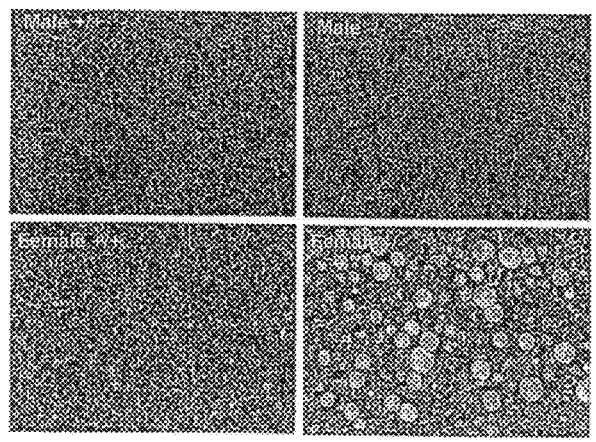
FIG. 4 illustrates liver histology for male and female of wildtype (CHDH+/+) or CHDH−/− genotype. Fat deposits (appearing as white space within the liver cells) accumulates in female CHDH−/− mice.

Tissues known to express CHDH, with the exception of liver (FIG. 4), appeared to be normal by assessment of gross histology and selected biochemical tests of organ function. FIG. 4 illustrates liver histology for male and female of wild-type (CHDH+/+) or CHDH-/- genotype. Fat deposits (appearing as white space within the liver cells) accumulates in female CHDH-/- mice.

Gross anatomical and histopathological examination at the light microscopy level of kidney, brain, testis, skeletal and cardiac muscle showed no differences between $CHDH^{-/-}$ and $CHDH^{+/+}$ mice. Hepatic lipid accumulation was observed in some, but not all, $CHDH^{+/+}$ and $CHDH^{-/-}$ animals; the presence of lipid did not correlate to either gender or genotype. All mice had some histopathologic signs of mild hepatic inflammation, likely due to endemic colonization by H. hepaticus bacteria, an extremely common pathogen in mouse colonies (Dewhirst et al., 1994; Fox et al., 1995) and present in the UNC Chapel Hill mouse colonies.

Mitochondria of liver, kidney, the CA3 region of the hippocampus in brain, skeletal muscle and heart, as well as kidney glomerular structure, were further examined using transmission electron microscopy. No morphologic changes were observed, except in skeletal muscle where a subset of mitochondria appeared swollen.

Though light microscopic examination of testis was not different between genotypes (FIGS. 5A and 5B), transmission electron microscopic examination of spermatic ultrastructure revealed that mitochondria in the midpiece of $CHDH^{-/-}$ sperm had malformed mitochondrial cristae and were enlarged/swollen compared to $CHDH^{+/+}$ mitochondria (FIGS. 5C-5F).

Example 6

Organ Function Analysis of $CHDH^{-/-}$ Mice

Biomarkers indicative of liver, kidney and muscle toxicity were assessed to determine effects of disruption of the CHDH gene. Plasma alanine transaminase (ALT) activity and total bilirubin concentration were used as indicators of liver toxicity, while blood urea nitrogen (BUN) concentration and plasma creatinine concentration were used as markers for kidney function. These values were measured at the Animal Clinical Chemistry and Gene Expression Facility located at the University of North Carolina at Chapel Hill using an automatic chemical analyzer (Johnson and Johnson VT250, Rochester, N.Y., United States of America). Plasma creatinine phosphokinase (CPK) activity was used as an indicator of muscle damage, and was measured using a Creatine Kinase-SL assay kit according to manufacturer's instructions (Diagnostic Chemicals Limited, Oxford, Conn., United States of America).

For urine collection and specific gravity measurement study, $CHDH^{+/+}$ and $CHDH^{-/-}$ mice were administered a subcutaneous injection of vasopressin (1.0 µg/kg AVP V2 receptor agonist desmopressin (dDAVP; Sigma, St. Louis, Mo., United States of America) at 8 AM. Animals were then housed in single mouse metabolic cages (cat #650-0315, Nalgene, Rochester, N.Y., United States of America) for 5 hours. Food and water were both withheld during this time. Animals were then anesthetized with Halothane as described previously. Any urine spontaneously voided during anesthetization was collected. Urine present in the bladder was collected by needle. Urine specific gravity was measured using a refractometer (AO Instrument Company, Buffalo, N.Y., United States of America) at the University of North Carolina at Chapel Hill Department of Laboratory Animal Medicine Veterinary and Technical Services Facility.

Selected tests of liver, kidney and muscle function were performed. Mean plasma ALT activity, a measure of hepatic damage, was unchanged (16.7 U/l in $CHDH^{-/-}$ vs. 19.1 U/l in $CHDH^{+/+}$ mice; p=0.64, n=10/group). Total plasma bilirubin concentrations, a measure of hepatic function, was unchanged (0.23±0.02 mg/dL in $CHDH^{-/-}$ vs. 0.24±0.03 mg/dL in $CHDH^{+/+}$ mice; p=0.71, n=10/group). Blood urea nitrogen (BUN) concentrations, a measure of renal function, was unchanged (13.0±0.8 mg/dL in $CHDH^{-/-}$ vs. 13.2±1.2 mg/dL in $CHDH^{+/+}$ mice; p=0.88, n=10/group). Both $CHDH^{+/+}$ and $CHDH^{-/-}$ mice had normal creatinine concentrations, a measure of renal function, that were less than 0.1 mg/d L. Additionally, urine specific gravity following water deprivation and vasopressin injection was unchanged in $CHDH^{-/-}$ mice (1.081±0.004, n=14) compared to $CHDH^{+/+}$ animals (1.080±0.008, n=12). Plasma creatine phosphokinase (CPK) activity, a measure of muscle damage, was unchanged (235±28 U/L in $CHDH^{-/-}$ vs. 165±25 U/L in $CHDH^{+/+}$ mice; p=0.07, n=12/group); these values are higher than CPK activity ranges previously reported for C57 mice (102-139 U/l; (Boehm et al. 2007)). All other measured values were within the published normal ranges for C57 mice (Downey et al., 2001; Narvaiza et al., 2006; Boehm et al., 2007; Wang et al., 2007). No differences were observed when data was analyzed for gender-specific effects on organ function.

Example 7

Tissue Ultrastructure Analysis of $CHDH^{-/-}$ Mice

Epididymal tissue was harvested from 8 to 10 weeks old $CHDH^{+/+}$ and $CHDH^{-/-}$ mice as described above. Tissue was fixed in 2% paraformaldehyde, 2.5% gluteraldehyde, 0.2% picric acid in 0.1 M sodium cacdylate, pH 7.2. Liver, kidney, brain and muscle tissues were harvested from animals anesthetized with Halothane as described above and then perfused via cardiac puncture of the left ventricle using a gravity perfusion system (IV-140, Braintree Scientific, Braintree, Mass., United States of America) with the same fixative. All tissues were stored in fixative until processed.

Tissue samples were subjected to centrifugation at 3000 rpm for 5 minutes, the supernatant removed and the tissue encapsulated in 2% agarose buffered with 0.1 M sodium cacodylate, pH 7.2. The agarose-encapsulated tissue was postfixed in 1% osmium tetroxide in 0.1 M sodium cacodylate, pH 7.2 for 1 hour. Following three 5 minute washes in deionized water, the samples were dehydrated through a series of ethanol baths, transferred to propylene oxide, infiltrated and embedded in Polybed-812 resin (Polysciences, Inc., Warrington, Pa., United States of America). Ultrathin sections were cut at 70 nm and post-stained with 4% aqueous uranyl acetate and 0.4% lead citrate. The grids were observed and photographed using a transmission electron microscope (Zeiss EM-10A, LEO Electron Microscopy, Inc., Thornwood, N.Y., United States of America) with an accelerating voltage of 60 kV.

Example 8

Concentration, Morphology and Motility of Sperm from $CHDH^{-/-}$ Mice

Eight to 10 week old $CHDH^{+/+}$ and $CHDH^{-/-}$ male mice were anesthetized with Halothane (Henry Schein, Inc.). A V-shaped incision was made beginning at the penis and extending out to the midline of the body. Testis and epididymis were excised from the animal and immediately placed in a 6-well tissue culture dish containing approximately 1 ml of M16 media (Sigma) in a well. All media, plates and tubes used were warmed to 37° C. prior to the dissection. Any plate or tube containing sperm, once isolated, was kept at 37° C. with 5% $CO_2$ for the duration of the experiment. The cauda epididymis was separated from the other structures and then placed in a 24-well plate containing 300 µl of fresh M16 media in each well. The cauda epididymis was then cut several times and the dish was incubated at 37° C. with 5% $CO_2$ for 15 minutes. Sperm concentration was determined by counting cells with a hemocytometer. Percent motility was determined by counting the number of progressively motile sperm per total number of sperm present using a hemocytometer. "Progressively motile sperm" refers to sperm that swim forward in a somewhat straight line. Sperm that were moving, but that were swimming in circles were classified as non-progressively motile.

Although they display normal mating behavior, $CHDH^{-/-}$ males are largely unable to sire litters. One out of ten $CHDH^{-/-}$ males fathered a litter of two pups. Female $CHDH^{-/-}$ mice had no reproductive impairment. There were no differences in sperm counts among $CHDH^{+/+}$, $CHDH^{+/-}$ and $CHDH^{-/-}$ males (FIG. 6). Normal sperm counts for C57/129 mixed mice are $21 \times 10^6$ per mL (Adham et al. 2001).

Figure 7:
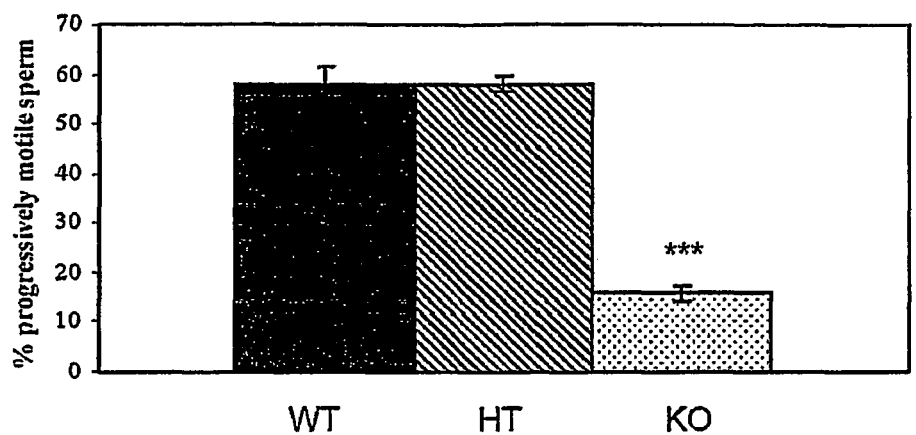
FIG. 7 is a bar graph showing percent progressively motile sperm in three different mouse lines. The mouse lines depicted are: wild-type mice (W; solid bar), mice in which one copy of the CHDH gene (CHDH+/−) has been knocked out (HT; hatched bar), and mice in which both copies of the CHDH gene (CHDH−/−) have been knocked out (KO; stippled bar). Sperm motility was significantly lower in the CHDH−/− mice.

The results indicate that $CHDH^{+/-}$ mice did not have any impairment in sperm motility (FIG. 7). $CHDH^{-/-}$ males had significantly decreased sperm motility, with only 16% of sperm classified as progressively motile (FIG. 7). In contrast, wildtype and heterozygous males had 58% progressively motile sperm and bred successfully. The exact cause of the impaired motility observed for the CHDH knock out mice has not been determined; however, the results shown in FIGS. 11-15 show electron microscopic and biochemical (MU, JC-1) evidence of mitochondrial dysfunction in the sperm of knockout mice.

Published results indicate that sperm motility depends on normal mitochondrial function (Kasai T, et al., 2002) Mitochondrial membranes must maintain an electrochemical gradient in order for oxidative phosphorylation and ATP generation to proceed. As stated before, CHDH is a mitochondrial enzyme localized to the inner membrane leaflet. A molecule of FADH is generated with oxidation of each choline molecule which, ultimately, results in the production of 2 ATP molecules through the electron transport chain (Kagawa et al., 1965).

Very high concentrations of betaine measured in mitochondria suggest that conversion of choline to betaine occurs at rapid rates in mitochondria and, therefore, is a major source of FADH, and perhaps an important source of energy for sperm motility (de Ridder and van Dam, 1973). To determine whether sperm motility can be restored through betaine supplementation, CHDH–/– mice were given drinking water supplemented to 2% betaine for 38 days. The supplementation experiment resulted in partial restoration of progressive sperm motility to approximately 30%. However, this was still significantly less than the motility of treated and untreated $CHDH^{+/+}$ and $CHDH^{+/-}$ males (FIG. 17B). Betaine supplementation did not have any effect on sperm concentration in $CHDH^{+/+}$, $CHDH^{+/-}$ or $CHDH^{-/-}$ mice (FIG. 17A).

Spermatozoa from $CHDH^{-/-}$ males had greatly impaired ability to reduce 3-(4,5-dimethyl thiazol-2-yl)-2,5-diphenyl tetrazolium bromide (MTT) compared to wildtype and heterzygous spermatozoa ($p<0.05$). Inner mitochondrial membrane potential ($\Delta\Psi m$), as assessed by JC-1 staining, was significantly decreased in $CHDH^{+/-}$ spermatozoa compared to $CHDH^{+/+}$ with $\Delta\Psi m$ in $CHDH^{-/-}$ sperm being significantly lower than both $CHDH^{+/+}$ and $CHDH^{+/-}$. Betaine supplementation did not change the amount of MTT reduction in $CHDH^{+/-}$ or $CHDH^{-/-}$ spermatozoa; however, supplementation did decrease MTT conversion in $CHDH^{+/+}$ sperm by 67% (FIG. 17C). Betaine supplementation had no effect on $\Delta\Psi m$ (FIG. 17D).

Example 9

Mitochondrial Function Analysis of $CHDH^{-/-}$ Mice

Sperm were isolated from the cauda epididymis as described above. An MTT (3-(4,5-dimethyl thiazol-2-yl)-2,5-diphenyl tetrazolium bromide) assay was conducted to measure mitochondrial function (Nasr-Esfahani, Aboutorabi et al. 2002) with the following modification: rather then visualizing positive MTT staining microscopically, MTT assays were conducted using a commercially available MIT assay kit (CellTiter 96 Non-radioactive Cell Proliferation Assay, Promega, Madison, Wis., United States of America) and cells were solubolized with the provided Solubolization/Stop Mix. 100 µL of isolated sperm were incubated in F10 media (Invitrogen Inc., Carlsbad, Calif., United States of America) in a 96-well plate with 15 µL of MTT solution at 37° C./5% $CO_2$ for 2 hours. Following solubolization, the absorbance of each sample was read at a wavelength of 562 nm using a BIOTEK® plate reader (BioTek Instruments Inc., Winooski, Vt., United States of America). Absorbance was normalized to the number of sperm assayed.

Mitochondria from liver, kidney, brain, skeletal and cardiac muscle and testis were isolated as described above and mitochondrial protein content was measured by Lowry assay. MTT assays for isolated mitochondria were performed in 96-well plates using the same MTT assay kit with some modification. An aliquot of each sample (approximately 10-20 µg mitochondrial protein) was incubated in 100 µL of assay buffer (AB; 110 mM KCl, 10 mM ATP, 10 mM $MgCl_2$, 10 mM sodium succinate, 1 mM EGTA in 20 mM MOPS, pH 7.5) and 15 µL MTT solution for 15 minutes at 37° C. with 5% $CO_2$. Reactions were terminated using the provided Solubolization Solution/Stop Mix and plates were read as described above. Absorbance was normalized to the amount of mitochondrial protein assayed.

To detect changes in mitochondrial membrane polarization, JC-1 staining was performed on sperm harvested from cauda epididymis (see FIGS. 8-11 and 13). Briefly, sperm were isolated from the cauda epididymis as stated above. Sperm were incubated with JC-1 dissolved in DMSO (Sigma) at a final concentration of 10 µg/mL in F10 media (Invitrogen Inc.) for 10 minutes at 37° C. with 5% $CO_2$. Following incubation, the sperm were transferred to a 1.5 mL microfuge tube and spun at 800×g for 3 minutes. The supernatant was discarded and sperm were gehtly resuspended in warm PBS. Additionally, sperm viability by staining sperm with a dye developed specifically to assess sperm viability (SYBR14; Live/Dead Sperm Viability Kit, Molecular Probes, Eugene, Oreg., United States of America) according to the manufacturer's instructions. 20 µl of each stained sample was examined with a fluorescence microscope (Olympus BX50, Olympus America, Inc., Center Valley, Pa., United States of America) and large band epifluorescence filters. JC-1 stained cells that fluoresced red, an indication of normal mitochondrial membrane potential, and fluoresced green when stained with SYBR14, indicating viable sperm with intact plasma membranes, were counted. Five fields of vision were counted for each sample and results expressed as percent of total cells.

JC-1 staining was also performed on mitochondria isolated from liver, kidney, brain, skeletal and cardiac muscle and testis. 10 μL of isolated mitochondria, approximately 100 μg of mitochondrial protein, were incubated with 1.72 mL of AB (see MTT assay) and 18 μL of 0.2 mg/mL JC-1 dissolved in DMSO for 10 min at room temperature protected from light. A mitochondrial sample from CHDH$^{+/+}$ liver, treated with valinomycin (1:200 final dilution) for 20 minutes, was used as a negative control. Fluorescence was measured in each sample using an excitation wavelength of 490 nm and an emission wavelength scan from 500 nm to 700 nm on a Hitachi F-2500 fluorescence spectrophotometer (Hitachi HTA, Pleasanton, Calif., United States of America). A peak at 595 nm corresponds to red fluorescence of J-aggregates. Fluorescent units were normalized to the amount of mitochondrial protein assayed.

Figure 16:
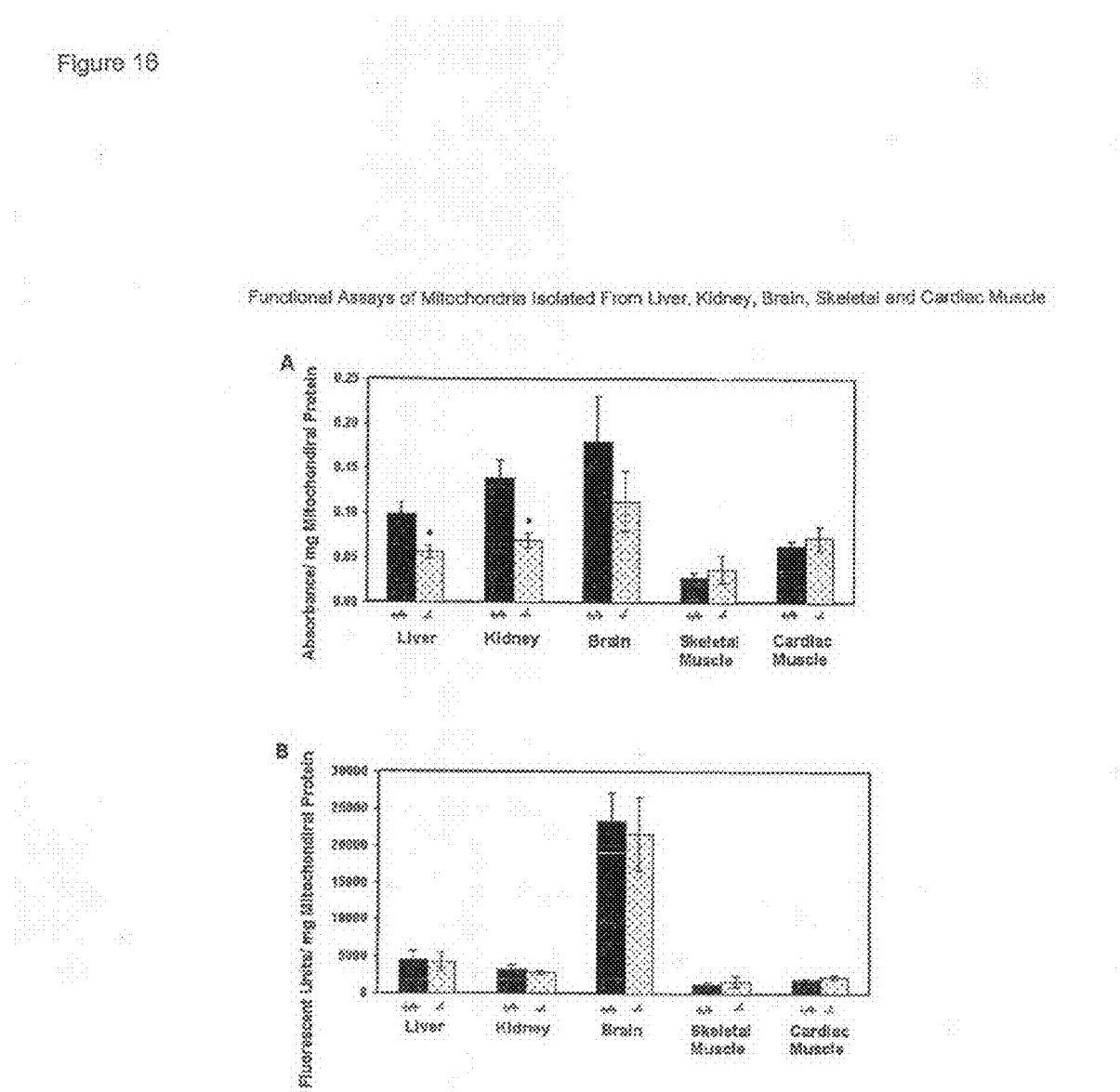
FIGS. 16A and 16B are bar graphs showing the results of functional assays of mitochondria isolated from liver, kidney, brain, skeletal and cardiac muscle.

Purified mitochondria from CHDH$^{-/-}$ liver, kidney and testis tissue had decreased MTT conversion (p<0.05) (FIG. 16A). There were no differences in brain, skeletal or cardiac muscle mitochondria MTT conversion. There were no genotype-specific differences in $\Delta\Psi m$ (FIG. 16B).

Example 10

Plasma Total Homocysteine Assay of CHDH$^{-/-}$ Mice

Mice were anesthetized with Halothane as described above. Blood from CHDH$^{+/+}$ and CHDH$^{-/-}$ animals was collected via cardiac puncture using heparin coated 20G needles and 3.0 mL syringes. Plasma was isolated by spinning samples at 400×g (2500 rpm) for 5 minutes at room temperature. Samples were derivatized using 7-fluorobenzofurazan-4-sulfonic acid (SBD-F) as described previously (Ubbink et al., 1991). 50 μL of each sample was injected and total plasma homocysteine concentrations were measured by high performance liquid chromatography (Microsorb-MV C18 (5 μm, 100 Å, 25 cm, Varian Inc., Palo Alto, Calif., United States of America); ProStar solvent delivery system (PS-210, Varian Inc.); and a fluorescence spectrophotometric detector (Varian Prostar model 360) with an excitation wavelength of 385 nm and an emission wavelength of 515 nm) at a flow rate of 0.5 mL/minute mobile phase (0.1 M ammonium acetate containing 3% methanol, pH 5.5) with a total run time of 20 minutes per sample. 10 μM cysteamine was used as an internal standard for the assay.

The results indicate that male CHDH$^{-/-}$ mice have significantly higher concentrations of plasma homocysteine than male wildtype mice. Homocysteine is removed by methylation to form methionine, which reaction is catalyzed by betaine homocysteine methyltransferase (BHMT) or by methionine synthase (MS). The first reaction does not proceed in the absence of betaine, and betaine supplementation has been employed as a treatment for elevated homcysteine (Lawson-Yuen and Levy, 2006; Olthof and Verhoef, 2005; Steenge et al., 2003; Wendel and Bremer, 1984). It is unclear why female knockouts did not have elevated homocysteine, although the dimorphism may reflect a difference in the relative contributions of the BHMT and MS pathways in males and females.

Example 11

SAM/SAH Assay Analysis of CHDH$^{-/-}$ Mice

S-adenosylmethionine (SAM) and S-adenosylhomocysteine (SAH) concentrations were measured in liver tissue of CHDH$^{+/+}$ and CHDH$^{-/-}$ animals using an HPLC method (Molloy et al., 1990; Shivapurkar and Poirier, 1983). The assay was performed on a Varian ProStar HPLC system (PS-210) using a Beckman Ultrasphere ODS 5 μm C18 column, 4.6 mm×25 cm (Fullerton, Calif., United States of America; cat#235329) at 55° C. with an online Gilson 118 UV/VIS detector (Middleton, Wis., United States of America). Samples were eluted with linear gradient of Solvent A (25 mM NaH$_2$PO$_4$—H$_2$O with 10 mM 1-heptanesulfonic acid, pH 3.2) and Solvent B (100% methanol containing 10 mM 1-heptanesulfonic acid) at a flow rate of 1.6 mL/min. 50 μL of each sample was injected for analysis.

There were no genotypic effects on SAM and/or SAH (Table 4).

Example 12

Statistical Analysis

Data were expressed as mean±standard error of the mean. Statistical differences between means were determined using JMP software, version 6.0 (SAS Institute, Cary, N.C., United States of America). ANOVA, Tukey-Kramer HSD, logistical regression and Student's t-test assuming equal variances were used to test differences. Wilcoxon Rank Sums test was performed to determine differences in hepatic lipid accumulation experiments. All tests were performed at α=0.05.

Discussion of Examples 1-12

The above Examples demonstrate, for the first time, the successful creation of a mouse in which the CHDH gene has been deleted. Fetuses from heterozygous matings were viable, grew normally, and had a normal lifespan. The most striking phenotype observed in these animals was severe asthenospermia in CHDH$^{-/-}$ males.

Deletion of CHDH greatly reduced activity in all tissues which normally express this gene (Table 1). Small residual activity detected probably reflects activity of other dehydrogenases that can use betaine as a substrate, likely cytosolic enzymes as mitochondrial betaine was not detectable in knockout mice (Table 2). Liver samples from CHDH$^{+/-}$ mice had 37% of the CHDH activity measured in CHDH$^{+/+}$ samples, suggesting that there is one copy of the CHDH gene present in mice and that it is biallelically expressed.

In all tissues studied, deletion of the gene resulted in extremely low concentrations of betaine; the small remaining amounts likely were derived from dietary betaine (AIN76A diet contains 70.35 nmol betaine/g diet) or from activity of dehydrogenases in cytosol. Betaine concentrations are usually millimolar in mitochondria from kidney, liver and testes, but in CHDH$^{-/-}$ little betaine was detected in mitochondria (Table 2). In tissues, CHDH and choline kinase compete for choline substrate (Zeisel et al. 1980), thus, in CHDH$^{-/-}$ mice choline concentrations increased (in testis and liver, choline concentrations nearly doubled in CHDH$^{-/-}$ animals), or the increased choline was phosphorylated forming PCho (in kidney, brain and testis).

CHDH$^{-/-}$ mice had significantly higher plasma tHcy concentrations than did their CHDH$^{+/+}$ littermates. tHcy is removed by three pathways: it can be methylated using betaine as a methyl donor, or methylated using methyltetrahydrofolate as a methyl donor, or condensed with serine to form cysthionine (Jacobsen, 1996). An accumulation of tHcy has been associated with an increased risk of cardiovascular disease (Glueck, Shaw et al. 1995; Melenovsky, Stulc et al. 2003) and, therapeutically, betaine has been employed as a treatment for elevated tHcy (Wendel and Bremer 1984; Steenge, Verhoef et al. 2003; Olthof and Verhoef 2005; Lawson-Yuen and Levy 2006). Based on the CHDH$^{-/-}$ mouse model, it appears predictable that individuals who harbor SNPs that decrease CHDH activity, possibly rs12676, would have higher plasma tHcy concentrations and may be at greater risk for developing cardiovascular disease.

In females, deletion of CHDH was associated with diminished PtdCho and, in females and males, SM (SM is formed from PtdCho) concentrations in liver. A major pathway for PtdCho synthesis is the methylation of phosphatidylethanolamine catalyzed by phosphatidylethanolamine-N-methyltransferase (PEMT); a gene that is induced by estrogen (Resseguie, Song et al. 2007). Although not wishing to be bound by any one theory, applicants speculate that CHDH deletion limited methyl groups for this pathway. However, applicants only observed a modest decrease (not statistically significant) in hepatic SAM concentrations in CHDH$^{-/-}$ mice (Table 4).

Abnormalities in several measures of liver, muscle and kidney function were not observed. Betaine is an important organic osmolyte in the glomerulus of the kidney, needed to concentrate urine and save free water (Miller et al. 1996). Despite having only 1.8% of the betaine concentrations found in CHDH$^{+/+}$ kidney tissue, CHDH$^{-/-}$ animals were able to normally reabsorb water in the kidney and did not produce dilute urine as we had predicted. Without being bound to one particular theory, applicants hypothesize that other organic osmolytes found in the glomerulus were able to compensate for the lack of betaine.

Spermatozoa function was severely compromised in CHDH$^{-/-}$ males. Homozygous males were largely infertile due to decreased motility of their spermatozoa. CHDH$^{+/-}$ males did not demonstrate any impairment in sperm motility, likely because developing sperm share cytosolic components during spermatogenesis (Braun, Behringer et al. 1989; Ventela, Toppari et al. 2003) and the products of choline oxidation (reduced equivalents, betaine) could be shared between cells. Indeed, applicants routinely use CHDH$^{+/-}$ mice to generate animals used in our studies.

Figure 5:
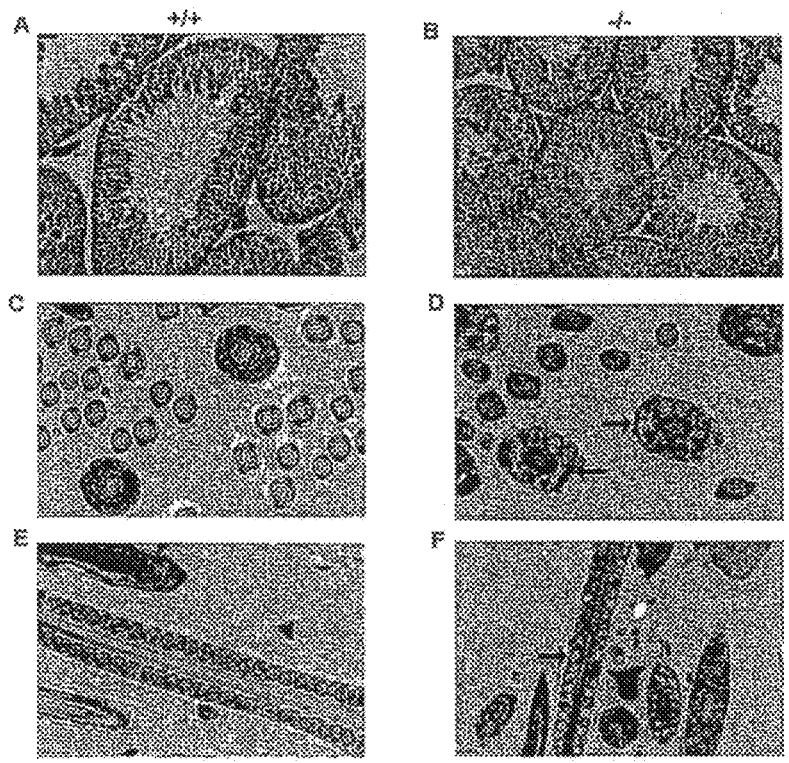
FIG. 5 shows testis histology and transmission electron microscopy of sperm in CHDH+/+ and CHDH+/− mice.
Figure 10B:
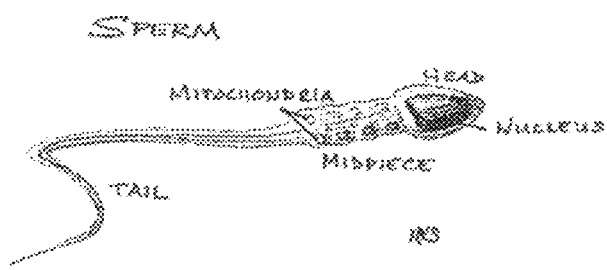
Figure 11:
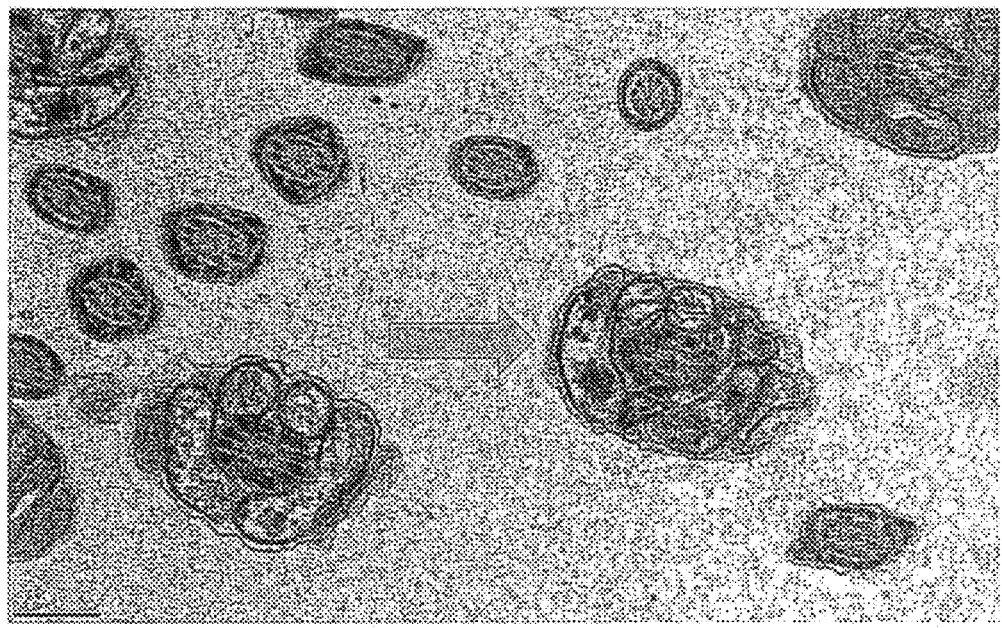
FIG. 11 is a photograph showing abnormal mitochondrial morphology of sperm taken from KO (CHDH−/−) mice using a transmission electron microscope (TEM). The mitochondria are swollen and distorted in CHDH−/− mice, but appear normal in CHDH+/+ mice.
Figure 12:
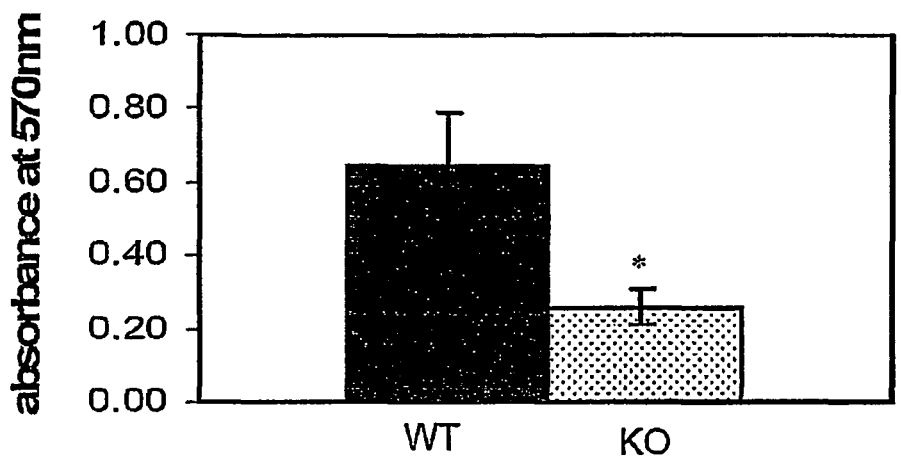
FIG. 12 is a bar graph showing the results of an MTT Assay for mitochondrial function in WT (CHDH+/+ (solid bar)) and KO (CHDH−/− (stippled bar)) mice. The MTT assay tests mitochondrial function in that mitochondria must be working to change the color of a dye. KO mice show diminished mitochondrial function relative to WT mice by MTT Assay.
Figure 13:
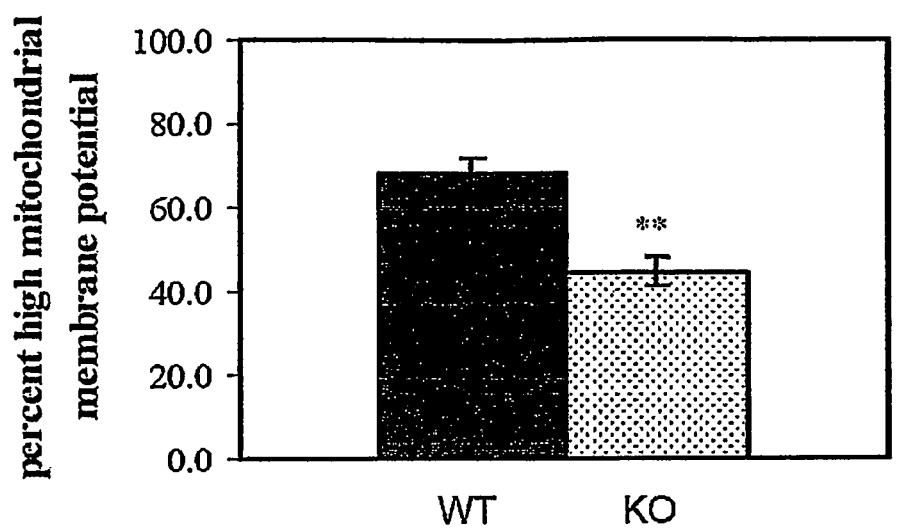
FIG. 13 is a bar graph showing the results of an assay for mitochondrial membrane potential using JC-1 staining of mitochondria taken from WT (CHDH+/+ (solid bar)) and KO (CHDH−/− (stippled bar)) mice. Mitochondrial membrane potential is maintained by ion pumps that must be working in the mitochondria. KO mice do not appear to maintain normal membrane potential in mitochondria relative to WT mice.
Figure 14:
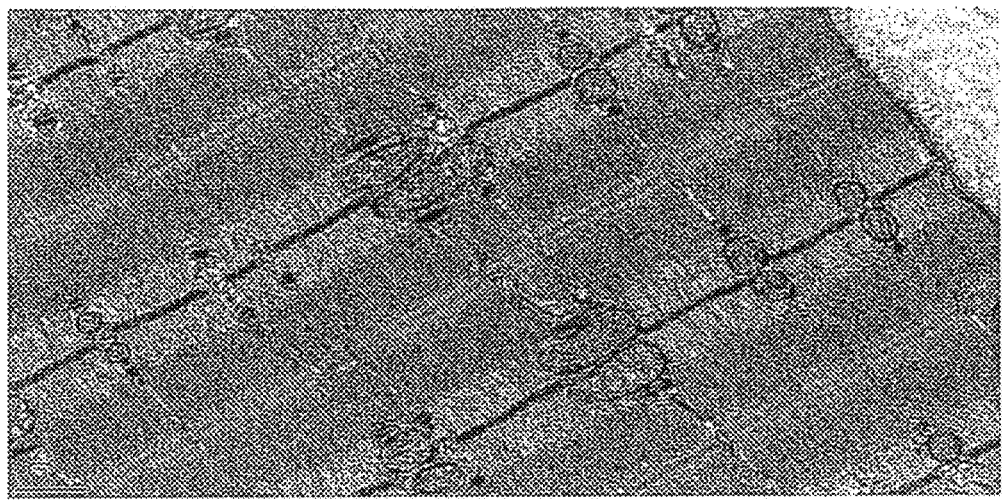
FIG. 14 is a photograph taken using a transmission electron microscope (TEM) showing skeletal muscle of INT (CHDH+/+) mice.
Figure 15:
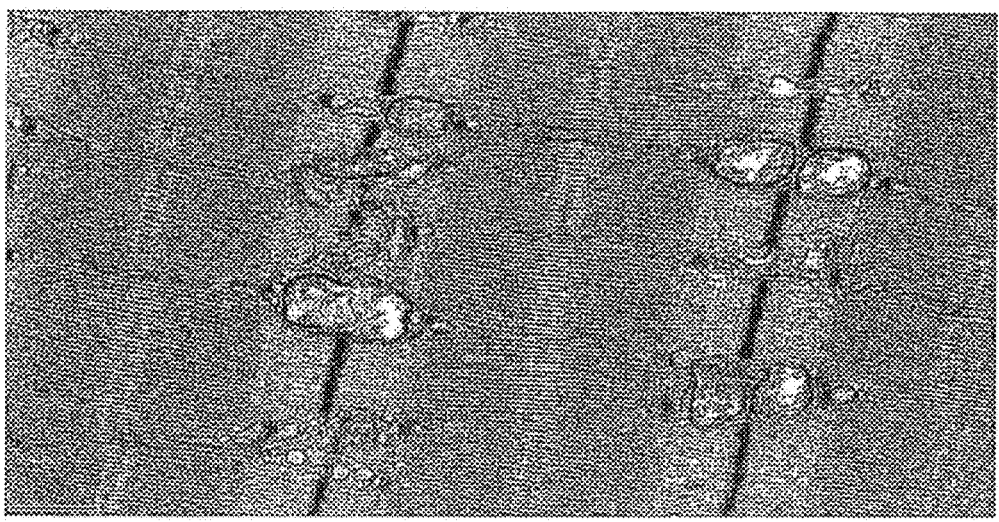
FIG. 15 is a photograph taken using a transmission electron microscope (TEM) showing skeletal muscle of KO (CHDH−/−) mice. The KO mice appear to have abnormal skeletal muscle mitochondria that are distorted and swollen.

A constant supply of ATP, both from mitochondrial oxidative phosphorylation (OXPHOS) and glycolysis, is required for sperm motility (Storey and Kayne 1975; Turner 2003; Ford 2006). When CHDH, an enzyme localized to the inner mitochondrial membrane, is absent, mitochondria in the spermatozoa midpiece appeared grossly abnormal when examined by electron microscopy (FIGS. 5 and 10-11). Additionally, these mitochondria could not reduce MTT normally (a mitochondria-dependent reaction) and could not maintain a normal membrane polarity (FIGS. 5 and 10-11). These results indicate that CHDH$^{-/-}$ sperm were not able to generate sufficient ATP through OXPHOS, and ATP generated by substrate-level phosphorylation during glycolysis is inadequate on its own to sustain sperm motility (M16 media contains 1M glucose).

The addition of choline to isolated rat hepatic mitochondria has been shown to increase resting state respiration (State II), accelerate ADP-stimulated respiration (State III) and slightly increase respiration in the presence of oligomycin (State IV) (Bruce Kristal, personal communication). Functional CHDH enzyme contains a FAD prosthetic group, which acts as an electron acceptor during the oxidation of choline to betaine aldehyde. Further oxidation of the betaine aldehyde intermediate to betaine, catalyzed by mitochondrial betaine aldehyde dehydrogenase, produces NADH (Zhang, Blusztajn et al. 1992). Therefore, oxidation of one choline molecule to betaine results in the generation of 5 ATP molecules by the mitochondrial electron transport chain (Kagawa, Wilken et al. 1965). Inhibition of electron transport chain Complex I with rotenone or Complex II using malonate decreases choline-stimulated mitochondrial respiration further demonstrating how choline availability and metabolism can influence mitochondrial function in tissues that normally express CHDH (Bruce Kristal, personal communication). Micromolar concentrations of betaine (Table 3) that are produced in mitochondria suggest flux through CHDH is very high in this organelle and, therefore, significant amounts of reduced equivalents must be produced making choline an important source of energy for the spermatozoa (de Ridder and van Dam 1973).

To test whether betaine was required for proper function of spermatozoan mitochondria, CHDH$^{+/+}$, CHDH$^{+/-}$ and CHDH$^{-/-}$ males were supplemented with betaine via drinking water for 42 days. This ensured that all sperm collected and assayed had developed in the presence of betaine. Betaine supplementation did not alter the number of sperm produced by males of any CHDH genotype, nor was there any effect on the motility of CHDH$^{+/+}$ or CHDH$^{+/-}$ spermatozoa. The asthenospermic phenotype of CHDH$^{-/-}$ males was improved, but not fully rescued, by betaine supplementation. No changes in mitochondrial function, as measured by MTT assay and JC-1 staining, were observed with betaine supplementation with one notable exception: MTT conversion in betaine-supplemented CHDH$^{+/+}$ spermatozoa was significantly decreased compared to untreated CHDH$^{+/+}$ sperm. Although these cells maintained $\Delta\Psi$m and did not show decreased motility, this result suggests that excess betaine might be toxic to mitochondria by decreasing the reductive capacity of these organelles. It is possible to speculate that the high amounts of betaine presumed to be in the testis due to supplementation might decrease CHDH activity in testis and sperm as betaine aldehyde has been shown to regulate CHDH activity by a negative feedback mechanism (Tsuge, Nakano et al. 1980). Taken together, these results indicate that while sperm motility is partially dependent on the presence of betaine, full motility requires intact choline oxidation, meaning production of reduced equivalents as well as the enzymatic product, and further study into the complex role of CHDH activity in spermatozoa motility is necessary.

Deletion of CHDH had important functional effects in mice; the presently described data suggest that mutations in CHDH could result elevated tHcy concentrations and male infertility in humans. The rs12676 SNP, located in the coding region of the human CHDH gene, occurs at a high frequency in the human population and renders pre-menopausal women more susceptible to developing fatty liver when they are ingesting a choline-deficient diet (da Costa, Kozyreva et al. 2006). Several other CHDH SNPs have been identified in humans but have unknown functional consequences. It is estimated that approximately 20% of human couples are infertile; in 50% of these couples the infertility was attributed to male factor infertility (World Health Organization, 1990). Of these, asthenospermia was diagnosed in 15%-17% of these men (Thonneau, Marchand et al. 1991; Maconochie, Doyle et al. 2004).

REFERENCES

All references cited in the specification, including but not limited to U.S. and foreign patents and patent application publications, scientific journal articles, and database entries (including all annotations presented therein), are incorporated herein by reference to the extent that they supplement, explain, provide a background for or teach methodology, techniques and/or compositions employed herein.

Adham, I. M., Nayernia, K., Burkhardt-Gottges, E., Topaloglu, O., Dixkens, C., Holstein, A. F., and Engel, W. (2001). Teratozoospermia in mice lacking the transition protein 2 (Tnp2). Mol Hum Reprod 7, 513-520.

Albright, C. D., Friedrich, C. B., Brown, E. C., Mar, M. H., and Zeisel, S. H. (1999a). Maternal dietary choline availability alters mitosis, apoptosis and the localization of TOAD-64 protein in the developing fetal rat septum. Brain Res Dev Brain Res 115, 123-129.

Albright, C. D., Tsai, A. Y., Friedrich, C. B., Mar, M. H., and Zeisel, S. H. (1999b). Choline availability alters embryonic development of the hippocampus and septum in the rat. Brain Res Dev Brain Res 113, 13-20.

Boehm, O., Zur, B., Koch, A., Tran, N., Freyenhagen, R., Hartmann, M., and Zacharowski, K. (2007). Clinical chemistry reference database for Wistar rats and C57/BL6 mice. Biol Chem 388, 547-554.

Buchman, A., Dubin, M., Moukarzel, A., Jenden, D., Roch, M., Rice, K., Gornbein, J., and Ament, M. (1995). Choline deficiency: a cause of hepatic steatosis during parenteral nutrition that can be reversed with intravenous choline supplementation. Hepatology 22, 1399-1403.

Chern, M. K., D. A. Gage, et al. (2000). "Betaine aldehyde, betaine, and choline levels in rat livers during ethanol metabolism." Biochem Pharmacol 60(11): 1629-37.

Chi-Shui, L., and Ru-Dan, W. (1986). Choline oxidation and choline dehydrogenase. J. Prot. Chem. 5, 193-200.

Cohen, G. and N. Kesler (1999). "Monoamine oxidase inhibits mitochondrial respiration." Ann N Y Acad Sci 893: 273-8.

Craciunescu, C. N., Albright, C. D., Mar, M. H., Song, J., and Zeisel, S. H. (2003). Choline availability during embryonic development alters progenitor cell mitosis in developing mouse hippocampus. J Nutr 133, 3614-3618.

da Costa, K. A., Kozyreva, O. G., Song, J., Galanko, J. A., Fischer, L. M., and Zeisel, S. H. (2006). Common genetic polymorphisms affect the human requirement for the nutrient choline. Faseb J 20, 1336-1344.

de Ridder, J., and van Dam, K. (1973). The efflux of betaine from rat-liver mitochondria, a possible regulating step in choline oxidation. Biochim. Biophys. Acta 291, 557-563.

Downey, P., Sapirstein, A., O'Leary, E., Sun, T. X., Brown, D., and Bonventre, J. V. (2001). Renal concentrating defect in mice lacking group IV cytosolic phospholipase A(2). Am J Physiol Renal Physiol 280, F607-618.

Einarsson, S., and Gustafsson, B. (1973). A case of epididymal dysfunction in boar. Andrologie 5, 273-279.

Ferguson, T. M., Atkinson, R. L., Bradley, J. W., and Miller, D. H. (1975). Reproductive performance of caged Beltsville Small White turkeys as affected by choline, bird density and forced molting. Poultry Science 54, 1679-1684.

Ford, W. C. (2006). "Glycolysis and sperm motility: does a spoonful of sugar help the flagellum go round?" Hum Reprod Update 12(3): 269-74.

Fox, J. G., Dewhirst, F. E., Tully, J. G., Paster, B. J., Yan, L., Taylor, N. S., Collins, M. J., Jr., Gorelick; P. L., and Ward, J. M. (1994). *Helicobacter hepaticus* sp. nov., a microaerophilic bacterium isolated from livers and intestinal mucosal scrapings from mice. J Clin Microbiol 32, 1238-1245.

Frezza, C., S. Cipolat, et al. (2007). "Organelle isolation: functional mitochondria from mouse liver, muscle and cultured fibroblasts." Nat Protoc 2(2): 287-95.

Haubrich, D. R., and Gerber, N. H. (1981). Choline dehydrogenase. Assay, properties and inhibitors. Biochem. Pharmacol. 30, 2993-3000.

Huang, S., and Lin, Q. (2003). Functional expression and processing of rat choline dehydrogenase precursor. Biochem Biophys Res Commun 309, 344-350.

Ikuta, S., K. Matuura, et al. (1977). "Oxidative pathway of choline to betaine in the soluble fraction prepared from *Arthrobacter globiformis*." J Biochem 82(1): 157-63.

Jacobsen, D. (1996). "Determinants of hyperhomocysteinemia: a matter of nature and nurture." Am J Clin Nutr 64(4): 641-642.

Jones, J. P., Meck, W., Williams, C. L., Wilson, W. A., and Swartzwelder, H. S. (1999). Choline availability to the developing rat fetus alters adult hippocampal long-term potentiation. Brain Res Dev Brain Res 118, 159-167.

Kagawa, T., Wilken, D. R., and Lardy, H. A. (1965). Control of choline oxidation in liver mitochondria by adenine nucleotides. J. Biol. Chem. 240, 1836-1842.

Kasai T, et al. Relationship between sperm mitochondrial membrane potential, sperm motility, and fertility potential. *Asian J Androl* 2002; 4: 97-103.

Kelly, T. L., O. R. Neaga, et al. (2005). "Infertility in 5,10-methylenetetrahydrofolate reductase (MTHFR)-deficient male mice is partially alleviated by lifetime dietary betaine supplementation." Biol Reprod 72(3): 667-77.

Koc, H., Mar, M. H., Ranasinghe, A., Swenberg, J. A., and Zeisel, S. H. (2002). Quantitation of choline and its metabolites in tissues and foods by liquid chromatography/electrospray ionization-isotope dilution mass spectrometry. Anal Chem 74, 4734-4740.

Lawson-Yuen, A., and Levy, H. L. (2006). The use of betaine in the treatment of elevated homocysteine. Mol Genet Metab 88, 201-207.

Lowry, O. H., Rosebrough, N. J., Farr, A. L., and Randall, R. J. (1951). Protein measurement with the Folin phenol reagent. J. Biol. Chem. 193, 265-275.

Maconochie, N., Doyle, P., and Carson, C. (2004). Infertility among male UK veterans of the 1990-1 Gulf war: reproductive cohort study. BMJ (Clinical research ed 329, 196-201.

Mann, P. J. G., and Guastel, J. H. (1937). The oxidation of choline by rat liver. Biochem. J. 31, 869-878.

Miller, B., H. Schmid, et al. (1996). "Determination of choline dehydrogenase activity along the rat nephron." Biol Chem Hoppe Seyler 377(2): 129-137.

Molloy, A. M., Weir, D. G., Kennedy, G., Kennedy, S., and Scott, J. M. (1990). A new high performance liquid chromatographic method for the simultaneous measurement of S-adenosylmethionine and S-adenosylhomocysteine. Biomedical Chromatography 4, 257-260.

Narvaiza, I., Aparicio, O., Vera, M., Razquin, N., Bortolanza, S., Prieto, J., and Fortes, P. (2006). Effect of adenovirus-mediated RNA interference on endogenous microRNAs in a mouse model of multidrug resistance protein 2 gene silencing. J Virol 80, 12236-12247.

Nasr-Esfahani, M. H., Aboutorabi, R., Esfandiari, E., and Mardani, M. (2002). Sperm MTT viability assay: a new method for evaluation of human sperm viability. J Assist Reprod Genet. 19, 477-482.

Niculescu, M. D., Craciunescu, C. N., and Zeisel, S. H. (2006). Dietary choline deficiency alters global and gene-specific DNA methylation in the developing hippocampus of mouse fetal brains. Faseb J 20, 43-49.

Ohta-Fukuyama, M., Y. Miyake, et al. (1980). "Identification and properties of the prosthetic group of choline oxidase from *Alcaligenes* sp." J Biochem 88(1): 197-203.

Olthof, M. R., and Verhoef, P. (2005). Effects of betaine intake on plasma homocysteine concentrations and consequences for health. Curr Drug Metab 6, 15-22.

Pomfret, E. A., daCosta, K., Schurman, L. L., and Zeisel, S. H. (1989). Measurement of choline and choline metabolite concentrations using high-pressure liquid chromatography and gas chromatography-mass spectrometry. Anal. Biochem. 180, 85-90.

Rajapakse, N., K. Shimizu, et al. (2001). "Isolation and characterization of intact mitochondria from neonatal rat brain." Brain Res Brain Res Protoc 8(3): 176-83.

Rendina, G., and Singer, T. P. (1959). Studies on choline dehydrogenase, I. extraction in soluble form, assay, and some properties of the enzyme. J. Biol. Chem. 234, 1605-1610.

Resseguie, M., J. Song, et al. (2007). "Phosphatidylethanolamine n-methyltransferase (PEMT) gene expression is induced by estrogen in human and mouse primary hepatocytes." FASEB J: in press.

Rozwadowski, K. L., G. G. Khachatourians, et al. (1991). "Choline oxidase, a catabolic enzyme in *Arthrobacter pascens*, facilitates adaptation to osmotic stress in *Escherichia coli*." J Bacteriol 173(2): 472-8.

Schwahn, B. C., Z. Chen, et al. (2003). "Homocysteine-betaine interactions in a murine model of 5,10-methylenetetrahydrofolate reductase deficiency." Faseb J 17(3): 512-4.

Schwahn, B. C., M. D. Laryea, et al. (2004). "Betaine rescue of an animal model with methylenetetrahydrofolate reductase deficiency." Biochem J 382(Pt 3): 831-40.

Shames, B., Fox, J. G., Dewhirst, F., Yan, L., Shen, Z., and Taylor, N. S. (1995). Identification of widespread *Helicobacter hepaticus* infection in feces in commercial mouse colonies by culture and PCR assay. J Clin Microbiol 33, 2968-2972.

Shivapurkar, N., and Poirier, L. A. (1983). Tissue levels of S-adenosylmethionine and S-adenosylhomocysteine in rats fed methyl-deficient, amino acid-defined diets for one to five weeks. Carcinogenesis 4, 1051-1057.

Steenge, G. R., Verhoef, P., and Katan, M. B. (2003). Betaine supplementation lowers plasma homocysteine in healthy men and women. J Nutr 133, 1291-1295.

Storey, B. T. and F. J. Kayne (1975). "Energy metabolism of spermatozoa. V. The Embden-Myerhof pathway of glycolysis: activities of pathway enzymes in hypotonically treated rabbit epididymal spermatozoa." Fertil Steril 26(12): 1257-65.

Thonneau, P., Marchand, S., Tallec, A., Ferial, M. L., Ducot, B., Lansac, J., Lopes, P., Tabaste, J. M., and Spira, A. (1991). Incidence and main causes of infertility in a resident population (1,850,000) of three French regions (1988-1989). Human reproduction (Oxford, England) 6, 811-816.

Tsuge, H., Y. Nakano, et al. (1980). "A novel purification and some properties of rat liver mitochondrial choline dehydrogenase." Biochim Biophys Acta 614(2): 274-84.

Turner, R. M. (2003). "Tales from the tail: what do we really know about sperm motility?" J Androl 24(6): 790-803.

Ubbink, J. B., Hayward Vermaak, W. J., and Bissbort, S. (1991). Rapid high-performance liquid chromatographic assay for total homocysteine levels in human serum. J Chromatogr 565, 441-446.

Ventela, S., J. Toppari, et al. (2003). "Intercellular organelle traffic through cytoplasmic bridges in early spermatids of the rat: mechanisms of haploid gene product sharing." Mol Biol Cell 14(7): 2768-80.

Wang, X., Meng, X., Kuhlman, J. R., Nelin, L. D., Nicol, K. K., English, B. K., and Liu, Y. (2007). Knockout of Mkp-1 enhances the host inflammatory responses to gram-positive bacteria. J Immunol 178, 5312-5320.

Wendel, U., and Bremer, H. (1984). Betaine in the treatment of homocystinuria due to 5,10-methylenetetrahydrofolate reductase deficiency. Eur. J. Pediatr. 142, 147-150.

World Health Organization. Prevention and Management of Infertility: Progress. Geneva: World Health Organization; 1990:15.

Yao, Z. M., and Vance, D. E. (1988). The active synthesis of phosphatidylcholine is required for very low density lipoprotein secretion from rat hepatocytes. J. Biol. Chem. 263, 2998-3004.

Zeisel, S. H. (2005). Choline: Critical Role During Fetal Development and Dietary Requirements in Adults. Annu Rev Nutr.

Zeisel, S. H. (2006). Choline: critical role during fetal development and dietary requirements in adults. Annu Rev Nutr 26, 229-250.

Zeisel, S. H., daCosta, K.-A., Franklin, P. D., Alexander, E. A., Lamont, J. T., Sheard, N. F., and Beiser, A. (1991). Choline, an essential nutrient for humans. FASEB J. 5, 2093-2098.

It will be understood that various details of the subject matter disclosed herein can be changed without departing from the scope of the presently disclosed subject matter. Furthermore, the foregoing description is for the purpose of illustration only, and not for the purpose of limitation.

What is claimed is:

1. A method for treating low sperm motility in a male human subject, comprising:

(a) providing a sample from a male human subject with low sperm motility;

(b) detecting in the sample the presence of at least one T allele of the single nucleotide polymorphism (SNP) rs12676; and (c) treating the subject with at least one T allele of the SNP rs12676 by administering an effective amount of choline, folate or betaine.

* * * * *

SEQUENCE LISTING

<160> NUMBER OF SEQ ID NOS: 3

<210> SEQ ID NO 1
<211> LENGTH: 30
<212> TYPE: DNA
<213> ORGANISM: Mus musculus

<400> SEQUENCE: 1
agggccacaa gtgtgggctg gctgaaactg                30

<210> SEQ ID NO 2
<211> LENGTH: 36
<212> TYPE: DNA
<213> ORGANISM: mus musculus

<400> SEQUENCE: 2

```
gctagcttga acccttttgaa gggtcttctc agactc                              36

<210> SEQ ID NO 3
<211> LENGTH: 19
<212> TYPE: DNA
<213> ORGANISM: mus musculus

<400> SEQUENCE: 3
acgcgtcacc ttaatatgc                                                  19
```